(12) United States Patent
Mercati et al.

(10) Patent No.: US 11,213,559 B2
(45) Date of Patent: Jan. 4, 2022

(54) FORMULATION FOR TREATMENT OF IRRITABLE BOWEL DISEASE

(71) Applicant: ABOCA S.P.A. SOCIETA' AGRICOLA, Sansepolcro (IT)

(72) Inventors: Valentino Mercati, Sansepolcro (IT); Anna Maidecchi, Sansepolcro (IT); Laura Capone, Rome (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 400 days.

(21) Appl. No.: 14/377,723

(22) PCT Filed: Feb. 8, 2013

(86) PCT No.: PCT/IB2013/051065
§ 371 (c)(1),
(2) Date: Aug. 8, 2014

(87) PCT Pub. No.: WO2013/118099
PCT Pub. Date: Aug. 15, 2013

(65) Prior Publication Data
US 2015/0023948 A1    Jan. 22, 2015

(30) Foreign Application Priority Data

Feb. 8, 2012 (IT) ............... RM2012A0043

(51) Int. Cl.
*A61K 36/534* (2006.01)
*A61K 36/886* (2006.01)
(Continued)

(52) U.S. Cl.
CPC .......... *A61K 36/534* (2013.01); *A23L 33/105* (2016.08); *A61K 31/715* (2013.01);
(Continued)

(58) Field of Classification Search
CPC .... A61K 31/715; A61K 31/733; A61K 33/44; A61K 33/105; A61K 36/18; A61K 36/23;
(Continued)

(56) References Cited

U.S. PATENT DOCUMENTS

2009/0180999 A1* 7/2009 Minatelli et al. .......... 424/93.45

FOREIGN PATENT DOCUMENTS

| CN | 1175460 A | * | 3/1998 |
| CN | 1349813 A | * | 5/2002 |
| CN | 1990030 A | * | 7/2007 |
| ZA | 201002664 A | * | 1/2011 |

OTHER PUBLICATIONS

Gourmet & Exotic Resin Incense: retrieved from internet: http://www.incensewarehouse.com/Resin-Resin-Burners_c_89.html. Retrieved on Jan. 1, 2016.*

(Continued)

*Primary Examiner* — Hong Yu
(74) *Attorney, Agent, or Firm* — Sterne, Kessler, Goldstein & Fox P.L.L.C.

(57) ABSTRACT

The present invention relates to an effective formulation for the treatment or the prevention of irritable bowel syndrome, a method for treating irritable bowel syndrome, and processes for preparing such formulations.

19 Claims, 6 Drawing Sheets

(51) Int. Cl.

| | |
|---|---|
| *A61K 36/515* | (2006.01) |
| *A61K 36/18* | (2006.01) |
| *A61K 36/28* | (2006.01) |
| *A61K 36/53* | (2006.01) |
| *A61K 36/235* | (2006.01) |
| *A61K 36/23* | (2006.01) |
| *A61K 33/44* | (2006.01) |
| *A61K 31/733* | (2006.01) |
| *A61K 31/715* | (2006.01) |
| *A61K 36/328* | (2006.01) |
| *A61K 36/288* | (2006.01) |
| *A61K 36/324* | (2006.01) |
| *A61K 36/185* | (2006.01) |
| *A23L 33/105* | (2016.01) |

(52) U.S. Cl.
CPC ............ *A61K 31/733* (2013.01); *A61K 33/44* (2013.01); *A61K 36/18* (2013.01); *A61K 36/185* (2013.01); *A61K 36/23* (2013.01); *A61K 36/235* (2013.01); *A61K 36/28* (2013.01); *A61K 36/288* (2013.01); *A61K 36/324* (2013.01); *A61K 36/328* (2013.01); *A61K 36/515* (2013.01); *A61K 36/53* (2013.01); *A61K 36/886* (2013.01); *A23V 2002/00* (2013.01); *A61K 2300/00* (2013.01)

(58) Field of Classification Search
CPC ...... A61K 36/28; A61K 36/53; A61K 36/185; A61K 36/235; A61K 36/288; A61K 36/324; A61K 36/328; A61K 36/515; A61K 36/534; A61K 36/886; A61K 2300/00; A23L 33/105; A23V 2002/00
See application file for complete search history.

(56) References Cited

OTHER PUBLICATIONS

Borneol Camphor: retrieved from internet: https://www.mermadearts.com/product_info.php?products_id=317. Retrieved on Jan. 2, 2019.*
Int'l Search Report and Written Opinion for PCT/IB2013/051065, dated Jul. 2, 2013.
Abascal & Yarnell "Combining herbs in a formula for irritable bowel syndrome" *Alternative and Complementary Therapies*, vol. 11, No. 1, pp. 17-23 (Feb. 2005).
Anonymous "Iberogast" *Wikipedia*, one page (Sep. 2011).
Anonymous "Irritable bowel syndrome" *Wikipedia*, 12 pages (Jan. 2012).
Goetz "La colopathie fonctionnelle" *Phytotherapie*, vol. 7, No. 6, pp. 323-326 (Nov. 2009).
Langhorst et al. "Randomized double-blind, double dummy, multicenter trial of a herbal preparation of myrrh, camomile and coffee coal compared to mesalamine in maintaining remission in ulcerative colitis" *Gastroenterology*, vol. 140, No. 5, suppl. 1, S264, BIOSIS database accession No. PREV201100402984, abstract only (May 2011).
Rahimi et al. "A review of the efficacy of traditional Iranian medicine for inflammatory bowel disease" *World Journal of Gastroenterology*, vol. 16, No. 36, pp. 4504-4514 (Sep. 2010).
Thakur et al. "Chlorophytum borivilianum: a white gold for biopharmaceuticals and neutraceuticals" *Current Pharmaceutical Biotechnology*, vol. 10, No. 7, pp. 650-666, EMBASE database accession No. EMB-2009637046, abstract only (Nov. 2009).
Wegener & Wagner "The active components and the pharmacological multi-target principle of STW 5 (Iberogast®)" *Phytomedicine*, vol. 13, suppl. 5, pp. 20-35 (Nov. 2006).
Williams & Slavin "Dietary fiber and other alternative therapies and irritable bowel syndrome" *Topics in Clinical Nutrition*, vol. 24, No. 3, pp. 262-271 (Jul. 2009).

* cited by examiner

FORMULATION FOR TREATMENT OF IRRITABLE BOWEL DISEASE

This application is the U.S. national phase of International Application No. PCT/IB2013/051065, filed 8 Feb. 2013, which designated the U.S.; and claims priority to IT Application No. RM2012A000043, filed 8 Feb. 2012; the entire contents of each of which are hereby incorporated by reference.

The present invention relates to an effective formulation for the treatment or the prevention of irritable bowel syndrome, a method for treating irritable bowel syndrome, and processes for preparing such formulations.

PRIOR ART

Irritable bowel syndrome (IBS) is a typical example of chronic functional disorders affecting the gastrointestinal system and is well known throughout the world, belonging to the class of functional disorders affecting the digestive system, that is to say without structural pathological alterations and/or biochemical anomalies. The physiopathology and aetiology of this disorder are unknown and therefore its diagnosis cannot be made by means of the usual medical tests (anatomical alterations or biochemical markers), but by means of the assessment of clinical symptoms including the occurrence of pain or recurring abdominal discomfort and changes to the intestinal functions, such as irregular bowel function, constipation and/or diarrhoea and/anomaly in the consistency of the stools.

Recent epidemiological data indicate that IBS may occur among the Western adult population with an incidence of 20%, whilst in Italy the incidence is much greater, equal to 30%. Based on official medical statistics, the female/male ratio among individuals suffering from IBS varies from 2:1 to 4:1. Women are therefore approximately 1.5 times more likely to suffer from IBS than men, are predominantly young and are affected by the form in which constipation predominates, whereas the sub-types of IBS in which alternating diarrhoea and constipation predominates are generally more common compared to the form with which constipation predominates. The syndrome is also mainly diagnosed in lower socioeconomic classes and in individuals less than 50 years of age.

IBS is a generally persistent condition that can become recurring or chronic; it therefore requires frequent recourse to a doctor, whether a general practitioner or a specialist, and the amount of work generated by patients suffering from IBS accounts for approximately one third of all visits to a gastroenterologist.

IBS can have a significant influence on the lifestyle of those who suffer from it, who consider the problem to be annoying, often painful, and constrictive. The patient experiences feelings of embarrassment and inhibition; in fact, this ailment not only affects the physical functions, but also the emotive functions: patients feel restricted and emotionally pained. Suffering from IBS means living with pain and abdominal bloating variable in frequency and intensity, but more frequently of high intensity. IBS is therefore an ailment that negatively influences daily activities and considerably worsens quality of life, with reduced productivity in work, repeated medical examinations, absence from school or work and subsequent high health costs in terms of healthcare and productivity.

Irritable bowel syndrome is a heterogeneous ailment for which it is not possible to identify a well-defined etiological factor, since it is caused by a combination of causes and effects. IBS presents a complex multifactorial framework in which the onset of the symptoms can also be linked to visceral hypersensitivity and alteration of gastrointestinal motility as well as genetic, psychological, environmental and behavioural factors, such that this ailment is also defined as a "biopsychosocial" dysfunction.

It seems as though it is caused by a combination of alterations to the motor functions and visceral sensitivity, often associated with affective disturbances. The changes to the bowel, which may present themselves in the form of constipation, diarrhoea or both at different times, have led to be conventional interpretation of IBS as a "motility disorder", but the motor changes are not able to fully explain the clinical picture. Recently, greater emphasis has been placed on the pathogenesis of the pain reported by these patients and there is significant evidence concerning the increased visceral sensitivity to stimuli, both harmful and physiological, in individuals affected by this syndrome. A largely accepted hypothesis is that, in genetically predisposed individuals, transient visceral damage leads to prolonged sensitisation of the neural circuitry of pain in spite of complete resolution of the initial pathological event.

Among the environmental/behavioural factors, it appears that stress and diet are the main causes of IBS, but with regard to dietary habits, the relationship between diet and IBS is complex. In certain cases, a link between meals and the onset of pain/abdominal bloating has been established, and in some cases the appearance of the symptoms is linked to the consumption of specific foods, although it is necessary to identify a definite and clear connection with a particular category of food before deciding on a restricted diet. In addition, a significant proportion of individuals being treated merely by dietary restrictions or fibre supplements continues to complain of symptoms and is subject to on-going various therapeutic approaches.

To conclude, the physiopathology of IBS is still highly debated. The current hypotheses are diverse and include dysmotility of the gastrointestinal tract, a change to visceral or central sensitivity, disorderly autonomous functions, release of mediators of inflammation and psychosocial disorders; it can therefore be deduced that these various mechanisms cannot be controlled sufficiently by a single pharmacological treatment.

The treatments of IBS are rather diverse and range from behavioural education to the use of new selective serotonin receptor modulators; however, there is not one reference drug for effective therapy of IBS.

Since IBS does not present specific anatomical characteristics and there are no reference biological markers (as there are for Chron's disease or for coeliac disease), the diagnosis of IBS is based on a careful evaluation of the clinical symptoms, including pain or chronic abdominal discomfort and changes to the intestinal functions (constipation, diarrhoea and/or anomaly in the consistence of the stools, although these may coexist with other symptoms affecting the entire gastrointestinal tract), and on the exclusion of other pathologies.

The simultaneous presence of various abdominal symptoms, including conflicting symptoms, was already noted more than a century ago when, in 1849, Cumming wrote "the intestine may be constipated or diarrhoeal in the same person and I confess to not knowing how to explain the cause of such conflicting symptoms". The first description of irritable bowel syndrome is attributed to Powell in 1818, but, until recently, was identified as a pathology that could only be diagnosed "by exclusion" of other pathologies and not by means of specific clinical criteria or parameters.

The first diagnostic clinical evaluations of IBS were initiated by means of the studies in the 1970s in the United Kingdom, which led in 1978 to the development of the Manning criteria, in which a questionnaire consisting of 15 questions is used and is aimed at differentiating, on the basis of symptoms, IBS from dysfunctions that could be interpreted as organic abdominal disorders.

International groups of experts, gathered to discuss the topic of gastrointestinal functional disorders, have developed diagnostic criteria known by the name of the Rome I, II and III criteria and have defined IBS as "a group of intestinal functional disorders in which abdominal pain is associated with defecation or change in intestinal habits or subjective perception of altered defecation". IBS is defined indifferently as a syndrome or as a dysfunction.

The current possibility of making a "positive" diagnosis of IBS based on defined and specific evaluation criteria of the symptoms and also on the exclusion of other possible pathologies is of fundamental importance, contributing to a correct classification of patients and to suitable therapeutic support as well as to greater awareness of IBS, including the epidemiology and the risk factors.

The typology and frequency of the symptoms characterising those patients affected by IBS as respondent to the characteristics listed in the box below have been defined by means of the Rome III criteria

---

ROME III DIAGNOSTIC CRITERIA FOR IBS

Abdominal pain or discomfort* recurring for at least
3 days of the month in the last 3 months combined
with two or more of the following symptoms:
1. relieved with defecation
2. onset associated with a change in frequency of stool
3. onset associated with a change in consistency of stool

*discomfort suggests an annoying sensation not described as pain. In cases of pathophysiological studies and clinical trials, a frequency of pain/discomfort of at least 2 days per week during the screening for assessment of the suitability of the subjects

---

Apart from being combined with changes to the bowel, abdominal pain/discomfort may also include other symptoms, such as flatulence or cramps, which are common in other disorders of the digestive system, such as dyspepsia.

The predominance of forms with diarrhoea or constipation has led to the division of irritable bowel syndrome into two main sub-groups: I BS-D (diarrhoea) and IBS-C (constipation), whilst the mixed form is named using the acronym IBS-M.

There is also the possibility that irritable bowel syndrome manifests itself following a gastrointestinal infection and in this case is classified as PI-IBS (post infective) and, compared to the other forms, may present itself by a change to the immunity function of the intestine (infiltration of lymphocytes and NO synthases in the stools).

The current pharmacological approach to irritable bowel syndrome reflects its multifactorial nature. Treatment is predominantly symptomatic and aspecific.

Before pharmacological treatment, patients with mild symptoms are initially advised as follows: lifestyle changes (increase in physical activity and adequate time for defecation are useful, particularly for constipated patients), dietary restriction (excessive consumption of caffeine, indigestible carbohydrates and increased consumption of lactose promote the development of IBS with diarrhoea) and integration of fibre, that is to say beneficial fibre, particularly soluble fibre, for all types of IBS. Such measures only bring marginal benefits or are unsuccessful in many patients, who continue to complain of symptoms and who are then subjected to different therapeutic/pharmacological alternatives.

Patients suffering from episodes of irregular abdominal pain of moderate intensity are often treated using drugs that reduce the contractility of the smooth intestinal musculature, spasmolytic drugs or anti-spastic drugs. These drugs have the aim of reducing gastrointestinal motility in order to reduce abdominal pain and cramps in all types of IBS, but require simultaneous treatment with pro-kinetics or laxatives in order to increase intestinal motility in cases of constipation. The category of anti-cholinergics includes $Ca^{+2}$ channel antagonists and peripheral opioid receptor antagonists. These are typically administered as required, therefore with the onset of pain, or before meals in order to prevent pain and the urge for defecation, which is typical in some patients with IBS. The majority of these agents are used for many years, but their use has been the subject of criticism and their side effects are often bothersome. Anticholinergic anti-spasmodics produce well-known adverse effects, and patients must be clearly advised of these: dry mouth, blurred vision and dizziness.

In recent years treatment has been focussed on the pharmacological treatment of the visceral sensitivity, and although the pharmacological principles of this hyperalgesia are unknown, the involvement of serotonin and its role in the sensitisation of the nociceptive neurones in inflammatory conditions has been suggested. This has led to the development of selective modulators of sub-types of serotonin receptors, such as tegaserod, 5-HT4 partial agonist, and alosetron, which is an agonist of 5-HT3 receptors.

Tegaserod, the only pro-kinetic that has been authorised by the FDA for the treatment of IBS with constipation, was withdrawn from the market in 2007 due to risks of severe cardiovascular events (ictus, myocardial infarction, angina pectoris) for short-term use. Other pro-kinetics commonly used in clinical practice include domperidone, metoclopramide, cisapride and renzapride, although these do not have specific indications for irritable bowel syndrome.

Alosetron, the first drug to have been approved for irritable bowel syndrome with diarrhoea in women, reduces gastrointestinal contractility, reducing colic transit and increasing absorption of liquids. Drugs in this category generally produce conflicting effects compared to 5-HT4 agonists (tegaserod). Alosetron was withdrawn from the market in the United States shortly after its commercial introduction due to an increased incidence of cases of ischaemic colitis (3 in every 1000 patients), which resulted in the need for surgical intervention and even led to death in a limited number of cases. However, the FDA has recently approved the use of this drug, with controlled distribution, for irritable bowel syndrome with diarrhoea. Meanwhile, conventional selective 5-HT3 inhibitor drugs, such as ondansetron, granisetron, cinansetron are frequently prescribed for IBS with diarrhoea, but also for many other different disturbances, such as nausea and vomiting. Alosetron is preferred for the specificity toward irritable bowel syndrome with diarrhoea and for the lower number of side effects, although its use is limited however due to the severe side effects that could cause ischaemic colitis, as already mentioned, inter alia.

α2-adrenergic receptor agonists, such as clonidine, are also able to increase visceral compliance and the pain associated with distension, whereas octreotide, an analogue of somatostatin, exerts selective anti-inhibitory effects on the afferent peripheral nerves, which, from the intestine, project over the spinal column and reduce the perception of rectal distension in patients affected by IBS.

Other treatments include psychopharmacological drugs, in particular antidepressants: selective serotonin reuptake inhibitors (SSRIs) and tricyclics (TCAs), at effective doses that are significantly lower compared to those used for the treatment of depression.

SSRIs have fewer side effects compared to TCAs and are used in particular in patients complaining of bowel changes with constipation since these drugs are able to increase intestinal peristalsis; these drugs do not reduce abdominal or visceral bloating however.

Other treatments include benzodiazepines (BDZs), which are directed to the etiological anxiogenic component and have a questionable effect in the treatment of IBS.

For the diarrhoeal component, loperamide is often used, but for short periods, due to the risk in the long term of developing a tolerance to the anti-diarrhoeal effect. Another opiate that is prescribed is codeine, but with considerable risks of sedation and dependence.

The assessment of probiotics for treating IBS has been summarised in meta-analysis studies, which have shown a modest improvement of bloating, abdominal pain and difficulty of intestinal movement. No specific probiotic strain has been found to be superior to the others, and combinations of bacteria are often used; many questions therefore remain open, such as what type of probiotic should be administered in what quantity and over what time.

Recently, psychotherapy (cognitive behavioural therapy, dynamic psychotherapy, hypnotherapy, relaxation techniques) has often been used among the therapies for treating IBS, but only for the more severe forms, associated with psychological disturbances or depressive or anxious states, although the effects of this therapy are only partial.

Currently, symptomatic drugs are often used to help those affected by IBS.

Such symptomatics include, in particular, spasmolytics, anti-diarrhoeals and laxatives.

There are also drugs that have a pharmacological effect on visceral hypersensitivity, although there is no specific coadjuvant that acts by means of non-pharmacological protective mechanisms.

It is therefore evident that the treatment of IBS still lacks useful and specific therapy with few side effects proportional to the low risk of the syndrome, but increased efficacy proportional to the severe disturbance that IBS causes to the quality of life of those affected by it.

SUMMARY OF THE INVENTION

The present invention provides a composition for the treatment and/or the prevention of irritable bowel syndrome (also referred to as irritable colon syndrome) comprising resins and/or extracts thereof, polysaccharides and/or plant extracts comprising polysaccharides, antioxidants and/or plant extracts comprising antioxidants of plant origin, a method for the treatment and/or the prevention of IBS, and a method for the preparation of said composition.

Given the controversies regarding the causes of IBS and the therapies to be implemented in order to treat the disorder, the development of new compositions able to prevent or to cure the disorder is rather complex since the prior art does not contain any teachings in agreement.

The authors of the present invention have selected components of plant/natural origin and have created a mixture of which the effect has been tested in in vitro tests and also with patients affected by IBS. The composition produced by the inventors and forming the basis of the present description has provided effective results comparable even to those obtainable with drugs that are currently preferred, without producing undesirable effects.

The composition however can also be used for preventative purposes, for example in those patients who have already suffered from IBS and who are at risk of redeveloping the disorder due to psychological, habitual reasons, etc.

The composition of the invention therefore comprises a set of components that are effective in controlling the symptoms of IBS, such as intestinal hyperalgesia and intestinal discomfort and irregularity, without being a specifically anti-spastic, anti-diarrhoeal or laxative composition.

The invention relates to the various embodiments of the composition, methods for preparing said composition, and also a method for treatment and/or prevention of IBS, which comprises the administration of the composition of the invention to patients requiring it, and a method for the preparation of said composition. The composition of the invention will be able to act on the inflammatory process by means of a local indirect protective and anti-inflammatory action, stemming from the protection, and also proposes to have an effect in the control of the symptoms of IBS, such as intestinal hyperalgesia and discomfort, by means of a protective effect of the intestinal mucus, which reduces irritation and irritability of said mucus, protecting the intestinal mucus against irritant attacks, for example by means of a barrier-like and antioxidant effect.

The composition according to the invention has been found to be useful in the regularisation of the bowel due to the reduced intestinal inflammation, without being a specifically anti-spastic, anti-diarrhoeal or laxative product.

DETAILED DESCRIPTION OF THE FIGURES

FIG. 1 shows the results of the assay for assessment of the mucus adhesion, which demonstrate good mucoadhesivity of the composition of the invention with respect to CaCo-2 gastrointestinal cells. The degree of mucoadhesivity obtained by the composition of the invention diluted 1:5 was 52%±4.6%, demonstrating that even a substantial dilution of the composition fails to have a significant influence on the mucoadhesive capacity of said composition with respect to the gastrointestinal cells.

FIG. 2 shows the resistance to washing with simulated gastric juices (2 ml/min). With regard to the second phase of the experiment, that is to say the phase of the experiment relating to the determination of the resistance of the mucoadhesive layer, formed by interaction between the resinous components and polysaccharides of the composition and the mucosal cells, the results obtained have demonstrated an interesting ability of these components to remain bio-adhered to the mucus, ensuring good mucoadhesivity for the first hour of contact, though remaining significant even after the second hour.

In fact, after 0.5 h, 1 h and 2 h, the percentages of mucoadhesion observed were 48.7±4.1% (0.5 h), 40.9±6.2% (1 h), and 29.5±4.6% (2 h).

FIG. 3 shows that the composition of the invention also has good scavenger activity with respect to oxidative stress comparable to that demonstrated by vitamin C. In addition, this action remains virtually constant from the second reading (60 minutes) taken. The composition of the invention destroys the formation of free radicals by 39% (±0.5) at all the doses analysed, demonstrating a seemingly "dose-independent" action. The composition of the invention does not promote the production of free radicals in a constitutive manner and does not demonstrate significant constitutive antioxidant action: a slight reduction of the radicals of approximately 10% (±0.5) after just 60 minutes of exposure to H202 is obtained. However, these results also demonstrate the same "dose-independent" trend found in the scavenger action, although with lower percentages. A table illustrating the activity is shown below.

The values indicated are expressed in mg/ml

The figure shows the following data

|  | % reduction of free radicals | | | |
| --- | --- | --- | --- | --- |
|  | 30 min | 60 min | 90 min | 120 min |
| Comp. inv. 0.5 mg/ml | 31.9 | 35.4 | 38 | 36 |
| Comp. inv. 10 0.25 mg/ml | 27.4 | 33 | 38.5 | 36 |
| Comp. inv. 10 0.125 mg/ml | 28.3 | 39.4 | 41.5 | 39.4 |
| Comp. inv. 10 0.078 mg/ml | 25 | 35.8 | 39.7 | 37.8 |
| vitamin C 0.15 | 38 | 44.8 | 48 | 47 |

FIG. 4 shows the trend of the abdominal pain scores in base conditions (B) and during the weeks of treatment (1-6) with the composition of the invention.

The progressive reduction of the pain scores, which reach a significant level (*=p<0.05) from the third week of treatment and continue to fall until the end of treatment, can be seen.

FIG. 5 shows the trend of the abdominal bloating scores in base conditions (B) and during the weeks of treatment (1-6) with the composition of the invention.

The progressive reduction of the bloating scores, which reach a significant level (*=p<0.05) from the fourth week of treatment and continue to fall until the end of treatment, can be seen.

FIG. 6 shows the trend of the wellbeing scores in base conditions (B) and during the weeks of treatment (1-6) with Colilen IBS.

The progressive reduction of the wellbeing scores, which reach a significant level (*=p<0.05) from the second week of treatment and continue to fall until the end of treatment, can be seen.

FIG. 7 shows the decrease in the classes of abdominal pain/discomfort linked to IBS during the time following administration of the composition of the invention (number of individuals on the ordinate and time expressed in weeks on the abscissa).

It can be seen how, from T0 to T6, the classes "severe", "moderate" and "mild" fall with a strong increase of the class "normal".

DETAILED DESCRIPTION OF THE INVENTION

Figure 1:
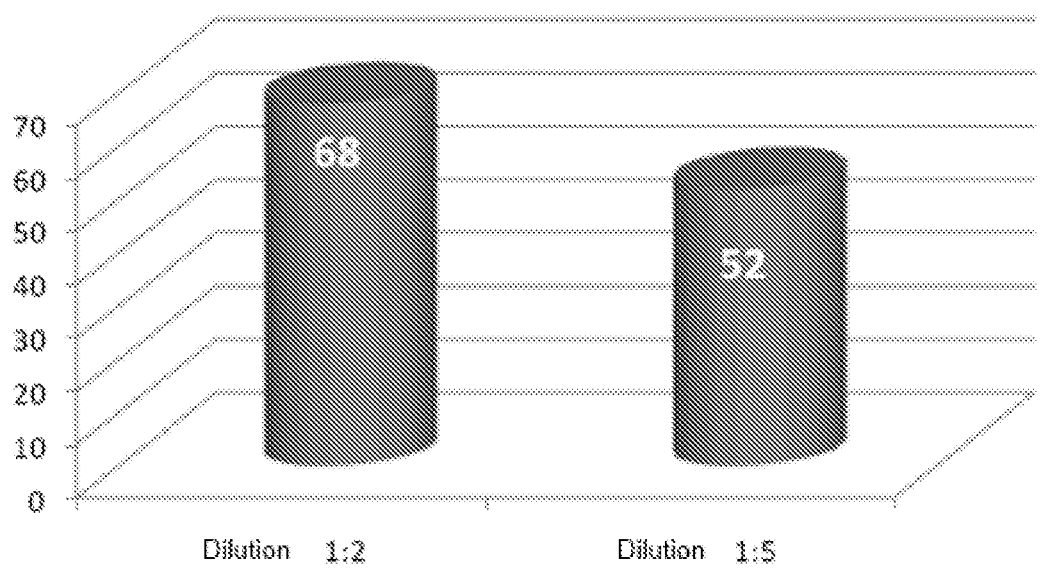

The invention describes a composition for use in the treatment and/or the prevention of irritable bowel syndrome comprising resins and/or extracts thereof, polysaccharides and/or plant extracts comprising polysaccharides, antioxidants and/or plant extracts comprising antioxidants and essential oils of natural or plant origin.

In fact, given its lack of undesirable effects, the composition described here can be used alone or in combination with other drugs for the treatment and/or the prevention of IBS. In a particularly advantageous form, the composition, given the lack of undesirable effects, can also be used for the prevention of IBS, for example in those patients suffering recurrently or for whom the disorder occurs in conjunction with specific psychological or physical states (for example periods of stress, etc.).

The composition described here comprises the above-listed active ingredients, such as active ingredients of plant origin or natural origin, that is to say not produced by chemical synthesis, but extracted from plants or natural products, such as resins produced by plants, mineral salts, etc.

In one embodiment, the active ingredients will be of plant origin (originating from parts of plants or from substances produced by the plants) and, in a specific embodiment, the composition or the products comprising it will all be of plant origin, except for the possible presence of mineral salts of natural origin rather than plant origin.

In an embodiment of the invention, the invention will comprise only components of plant origin (originating from parts of plants or from substances produced by the plants).

According to the present invention, in accordance with the scientific literature, resins of plant origin in particular are understood to mean oleo-gum resins, plant exudates that can be secreted by the plants physiologically or, more often, in response to mechanical traumas (incisions, cuts) or to stress (attack of pathogens) formed by a complex group of solid, translucent, occasionally liquid, water-insoluble, alcohol-soluble, acetone, ether and chloroform substances.

Such resins contain complex mixtures of alcohols or aliphatic acid, lignans, resin acids, resinotannols, esters and resins (that originate from processes of polymerisation or oxidation of terpenes of essential oils), etc.

From a chemical point of view, many different components are found in the resins: alcohols or aliphatic acids of various carbon chain length, free aromatic acids, resin acids, monoterpene alcohols, diterpene alcohols, triterpene alcohols, resinols, phenolic compounds belonging to the family of sterols, etc.

According to the present invention, the resins for example can be represented by incense, myrrh, or mixtures thereof.

A person skilled in the art will, however, be able to identify further resins other than those indicated herein easily be analogy.

The composition may contain such resins in pulverised or granulated form, or in the form of dry extract and/or lyophilised extract and/or fractions of said extracts.

The forms in which these resins and their extracts can be used for the preparation of compositions for oral administration are known in the literature, and a person skilled in the art will not require further teachings in this sense.

By way of non-limiting example, when preparing an extract, the resin can be treated with 20%, or 30%, or 40%, or 50%, or 60%, or 70%, or 80% hydroalcoholic solutions; the alcohols can be methanol, ethanol, isopropanol; in a specific embodiment, ethanol is used. The alcoholic extract obtained is subjected to filtration, concentration and desiccation to provide the corresponding dry extract.

The dry product obtained can be pulverised, granulated or treated by suitable mixing with the other components.

The resins, apart from assisting the production of a barrier effect on the mucus provided by the composition described here, as demonstrated in the experiments sections, also allow other components of the composition to remain adhered, over longer periods of contact, to the irritated epithelium, thus preventing rapid washing off by biological liquids, therefore enabling the composition to provide its effect over longer periods of time in an improved manner.

The polysaccharides according to the invention are polysaccharides present in natural products, or in plant extracts or obtainable from plants.

In one embodiment, these polysaccharides are of plant origin and are represented by macromolecular polysaccharides that, upon contact with water, form colloidal solutions or gels and can also be defined as plant hydrocolloids.

These polysaccharides are normal constituents of the plant cells preserved in predefined histological structures. They are polymers of sugars and are characterised by good stability, non-toxicity, hydrophilic properties and biodegradability.

A non-limiting example of polysaccharides that can be used in the present invention is given by polysaccharides extracted from Aloe vera, camomile, althea and other plants rich in polysaccharides.

In one embodiment, plant extracts comprising polysaccharides, such as (but not limited to) extracts of Aloe vera, camomile, althea and other plants rich in polysaccharides, can be used directly.

Without being bound to the theory, it is considered that the polysaccharides in the composition of the invention can assist the barrier effect and the mucoadhesivity of said barrier.

In accordance with an embodiment of the present invention, the composition will comprise an extract of Aloe vera.

In one embodiment, said extract is an extract of dehydrated leaf gel or other extracts rich in polysaccharides.

In a specific embodiment of the invention, as parts of the plant, the dehydrated leaf gel will be used for the Aloe, the inner flowers or ligulates will be used for the camomile, the roots will be used for the althea, and the leaves will be used for the lemon-balm. For all components listed above, use in the form of dry extract and/or lyophilised extract and/or fractions of such extracts is suitable.

The composition also comprises antioxidant substances of natural or plant origin, such as plant polyphenols or extracts comprising plant polyphenols.

In accordance with a non-limiting example, antioxidants extracted from camomile or lemon-balm can be used in the present composition. In one embodiment, plant extracts comprising antioxidants, such as extracts of camomile, lemon-balm and the like, can be used directly.

In a specific embodiment, the composition will comprise resins and/or extracts thereof selected from the group comprising incense and myrrh; polysaccharides selected from polysaccharides extracted from Aloe vera, camomile, althea and/or plant extracts comprising polysaccharides selected from extracts of Aloe vera (leaf gel), camomile (flowers), althea (roots); antioxidants selected from antioxidants extracted from camomile, lemon-balm leaf; plant extracts comprising antioxidants selected from extracts of camomile flowers and lemon-balm leaf.

In one embodiment, the composition comprises the following as active ingredients: lyophilised extract of incense, extract of Aloe vera (for example dehydrated leaf gel), extract of althea mucilages, extract of camomile flower and extract of lemon-balm leaf.

In addition, the composition may comprise one or more further plant or natural components selected by a person skilled in the art and having activity suitable for further assisting the effect of relieving IBS, such as: natural and/or plant emollient, digestive, pro-kinetic, cholagogic, carminative, prebiotic, relaxing, excipient, preserving and wetting substances. A non-limiting example of such substances can be represented by extract of gentian root, boldo leaf, milk thistle fruit, artichoke leaf, dandelion root, rosemary leaf, anise fruit, mint leaf, marjoram leaf, cumin fruit or seed, caraway fruit, coriander fruit, plant charcoal, ginger root, fennel fruit and inulin.

The composition according to the invention may comprise said resins and/or extracts thereof in a percentage in weight between 30 and 60%.

The composition may comprise said polysaccharides and/or plant extracts comprising polysaccharides in a percentage in weight between 12 and 22%.

The composition may comprise said antioxidants and/or plant extracts comprising antioxidants in a percentage in weight between 35 and 65%.

A non-limiting example of the composition according to the invention comprises incense powder approximately 50%

Aloe vera gel approximately 15% lyophilised camomile flower extract approximately 15% powder lemon-balm leaf approximately 45%

In accordance with a further example, the composition may comprise:

dry incense extract approximately 30%

Aloe vera gel approximately 20% camomile flower powder approximately 25% lyophilised lemon-balm leaf extract approximately 25%

In general, the composition may comprise:

dry incense extract approximately 30-60%

Aloe vera gel approximately 15-20% camomile flower powder approximately 15-25% lyophilised lemon-balm leaf extract approximately 25-45%

The composition can be formed by the above-mentioned components and, optionally, by an essential plant oil and possibly excipients when present in a formulation.

Any whole number included in the ranges described above are to be considered as described in the present invention together with the two numbers limiting the ranges, for example when the range described is 15-20%, this is intended to mean that the invention describes the embodiments comprising 15, 16, 17, 18, 19, and 20% of the extract.

The same is true for the ranges 30-60, 12-22, 35-65, 15-25 and 25-45 stated above.

In a specific embodiment, the composition of the invention comprises said resins and/or extracts thereof in a percentage in weight from 20 to 30%; said polysaccharides and/or plant extracts comprising polysaccharides in a percentage in weight from 7 to 13%; and said antioxidants and/or plant extracts comprising antioxidants in a percentage in weight from 45 to 55%.

As already indicated above, every time the present description provides a numerical range, all the whole numbers and the decimal numbers to two decimal places that exist within this range, including the limits, are also considered described at the same time and explicitly. The range is indicated merely so as to avoid long numerical lists that a person skilled in the art will in any case know to include in ranges such as those listed above.

In a specific embodiment, a daily or bi-daily dosage, for example divided into at least 3, 4, 5 or more units of administration of approximately 2-3 g of active ingredients of composition, may comprise:

COMPOSITION EXAMPLE 1 lyophilised resin incense extract, approximately 500-800 mg,
dehydrated Aloe vera leaf gel, 180-300 mg,
lyophilised camomile flower extract, 70-170 mg,
lemon-balm leaf, 800-1250 mg,
fennel essential oil, 40-60 mg,
cumin fruit or seed powder, 270-400 mg Further composition examples according to the invention are stated below:

COMPOSITION EXAMPLE 2 lyophilised resin incense extract, approximately 500-700 mg,
dehydrated Aloe vera leaf gel, approximately 180-300 mg,
lyophilised camomile flower extract, approximately 70-170 mg,
lemon-balm leaf, approximately 900-1150 mg,
fennel essential oil, approximately 40-60 mg,
coriander fruit powder, approximately 270-400 mg.

COMPOSITION EXAMPLE 3 resin incense powder, approximately 680-750 mg,
dehydrated Aloe vera leaf gel, approximately 440-520 mg,
lyophilised camomile flower extract, approximately 650-750 mg,
lemon-balm leaf, approximately 450-510 mg,
fennel essential oil, approximately 15-25 mg.

COMPOSITION EXAMPLE 4 lyophilised resin incense extract, approximately 440-520 mg,
dehydrated Aloe vera leaf gel, approximately 900-1000 mg,
lyophilised camomile flower extract, approximately 520-620 mg,
lemon-balm leaf, approximately 300-400 mg,
marjoram essential oil, approximately 15-25 mg.

COMPOSITION EXAMPLE 5 lyophilised resin incense extract, approximately 80-140 mg,
resin incense powder, approximately 200-280 mg,
dehydrated Aloe vera leaf gel, approximately 80-140mg,
impalpable dandelion powder, approximately 1600-2000 mg,
lyophilised camomile flower extract, approximately 80-140mg,
lemon-balm leaf, approximately 50-120 mg. COMPOSITION EXAMPLE 6
lyophilised resin incense extract, approximately 400-550 mg,
resin incense powder, approximately 200-300 mg,
dehydrated Aloe vera leaf gel, approximately 200-300 mg,
lyophilised camomile flower extract, approximately 100-160 mg,
lemon-balm leaf, approximately 1000-1500 mg.

In accordance with the present description, the term "comprising" can be substituted by the term "constituted by" in the definition of the compositions provided above by way of example.

The exemplary compositions can therefore also be understood as being constituted by the above-listed active ingredients, and may also comprise suitable excipients for the formulation thereof.

The application therefore relates to compositions comprising or consisting of the above-listed active ingredients or as described in the present description, optionally also comprising excipients suitable for the desired formulation as described below.

It is evident that the administration dosage can be adapted in accordance with the age, the weight, the sex, and the state of health of the subject. The compositions described here may also comprise one or more pharmaceutically acceptable excipients or one or more of the additional components listed above.

The compositions as described here may also be diluted in suitable excipients allowing production in liquid form or semi-liquid form (such as suspensions, solutions, emulsions), for example water, fruit juice or any other excipient suitable for production of pharmaceutical formulations and present in non-liquid or semi-liquid state for oral administration.

It is to be understood, within the scope of the present description, that, with regard to the embodiments in which the components of the composition are indicated, the term "comprises/comprising" can also be substituted by the term "consists/consisting of".

In accordance with the present invention, the composition can be used in capsule form, tablet form, granule form, powder form, syrup form, elixir form, hard gelatine capsule form, soft gelatine capsule form, suspension form, emulsion form or solution form in accordance with the methods known to a person of average skill in the art.

In particular, in the solid embodiments, powders of said plants compressed in the form of extracts or "products extracted from" can be used as excipients in the composition described here.

In a specific embodiment, the composition as described here, in any of the embodiments described above, may be present in the form of a pharmaceutical composition, that is to say may comprise ingredients of pharmaceutical ability, or may be in a dietary supplement for special purposes or in a medical device, or may be inserted therein.

The composition according to the present description can be produced in the form of a pharmaceutical composition or in the form of a medical device in accordance with any of the classes described in Medical Device Directive 9342EEC (which also includes substances and not just "devices" in the mechanical sense of the word), or in the form of a medical food, a dietary supplement or in any form in accordance with the regulations of the country in which said composition is produced.

For the preparation of the pharmaceutical compositions, the mixture of the extracts is formulated in suitable dosage units with one or more pharmaceutically acceptable excipients and/or additives. Pharmaceutical compositions in capsule form, tablet form, hard gelatine capsule form, or soft gelatine capsule form for oral administration may be in the form of a single daily dose or in the form of fractions of a single daily dose (for example 2, 3, 4, 5, 6 or more capsules, tablets or gelatines can be administered over a single day in accordance with the judgement of the treating doctor), and may contain excipients included conventionally, for example binding agents, such as arabic gum, gelatine, adragant gum and/or polyvinylpyrrolidone, diluting agents, for example lactose, sucrose, polyalcohols, dibasic calcium phosphate; disintegrants, such as maize starch, rice starch, potato starch, sodium starch glycolate, lubricating crospovidone, for example magnesium stearate, talc, polyethylene glycols, slip agents such as colloidal silica, and pharmaceutically acceptable wetting agents and surfactants, for example sodium lauryl sulphate or granulated extracts of said plants. The tablets can be coated by methods well known in standard pharmaceutical practice.

The composition can also be produced in liquid form or semi-liquid form, suspension form, emulsion form or solution form for oral administration and may optionally contain natural flavouring agents that provide said composition with an agreeable taste.

The composition in powder or granulate form can be pre-dosed in suitable containers and ready for use or for ingestion in this form or can be provided so as to be resuspended in a suitable liquid such as water or tea, etc. in this case too, the composition may contain natural flavouring agents that provide said composition with an agreeable taste.

The present invention has been described thus far with reference to some of its embodiments. It is understood that other embodiments may also exist that address the same inventive concept and are all included within the scope of protection of the claims as disclosed hereinafter.

The invention also relates to a method for the treatment and/or the prevention of IBS comprising the administration of the composition described here to an individual requiring it.

The method comprises the administration of one or more doses per day of the composition over a period varying from one or more weeks in accordance with the prescription of the treating doctor.

Given the high tolerance demonstrated for even high doses of the composition (see the examples below), the treating doctor may decide to prescribe therapy without running risks of overdosing following the teachings of the present description and in accordance with the requirements of the patient and of the common medical knowledge.

In one embodiment, the method comprises the administration of 2-3 grams, for example 2, 2.1, 2.2, 2.3, 2.4, 2.5, 2.6, 2.7, 2.8, 2.9, or 3 grams of active ingredients per day, for example divided into at least three single doses for a period of at least one week up to a period of 3-6 weeks or more.

It is evident that the administration may comprise different doses in accordance with the general state of health, the weight, the sex and the age of the patient.

The composition of the invention can also be administered in combination with other drugs commonly used for the treatment of IBS as an adjuvant of the treatment.

In one embodiment, the composition can be administered for example in combination with drugs aimed at treating a disorder believed to be the cause of clinical features of IBS.

In accordance with a non-limiting example of the method for treating or preventing IBS described here, a daily dose that uses any of the compositions stated above by way of example can be administered, with administration of such compositions once or twice per day for a period of time of 3 weeks or 6 weeks or another duration.

This dose can be divided, as in the examples on patients below, into 6 tablets (cp) administered 2 at a time three times per day approximately one hour before meals.

In addition, the invention relates to a method for preparing a composition according to the invention, in which said resins and/or extracts thereof, in which said polysaccharides and/or plant extracts comprising polysaccharides, and in which said antioxidants and/or plant extracts comprising antioxidants are mixed together, optionally together with one or more of the additional components described above and/or one or more excipients and/or one or more flavouring agents in a single step or in successive steps.

The mixing techniques selected shall be suitable for the form in which the composition is to be produced, that is to say at least one step of pressing, etc. will also be present if it is desired to produce tablets or pills.

For example, the extracts as described above can be mixed together by means of the known high shear mixer technology, which allows perfect homogenisation of the ingredients, even with the addition of small percentages of ingredients in liquid form (for example essential oils), which are sprayed onto the moving powder mass. Encapsulation or other processing steps is/are then carried out using conventional technology.

EXAMPLES

1. Pre-Clinical Tests of Efficacy on Irritable Bowel Syndrome

In vivo evaluation of the efficacy of the composition of the invention in protection of the intestinal mucosa To test in vivo the efficacy of the composition of the invention, said composition was formulated in capsules and was assessed in terms of its ability to protect the susceptibility of the intestinal mucosa to irritating stimuli. Based on the presumed mechanism of the product to act on the inflammatory component of IBS (supported only recently by the literature) by means of a local, indirect protective and anti-inflammatory action also stemming from mucoadhesion, an experimental model of inflammatory colitis, not specific for IBS, was selected.

The study was carried out on a model of colitis induced by acetic acid, as described by McPherson B R, Pfeiffer C J (1978) Experimental Production of Diffuse Colitis in Rats. Digestion;17:135-150; Mousavizadeh K, Rahimian R, Fakhfouri G, Aslani F S, Ghafourifar P. (2009) Anti-inflammatory effects of 5-HT receptor antagonist, tropisetron on experimental colitis in rats. Eur J Clin Invest.;39(5):375-83; Noronha-Blob L, Lowe V C, Muhlahauser R O, Burch R M. (1993) NPC 15669, an inhibitor of neutrophil recruitment, is efficacious in acetic acid-induced colitis in rats. Gastroenterology, 104:1021-9.

The animals were treated so as to induce intestinal inflammation (4% acetic acid via rectal insufflation) and, after one hour were treated with the composition of the invention as described in the general formula on page 16 and according to composition example 1 (data obtained comparable, data reported under composition example 1), or dexamethasone (reference drug).

Each group was formed by 10 rats in accordance with the following schema

1. Rats without colitis, treated with vehicle 10 ml/kg, (p.o.);
2. Rats with colitis, treated with vehicle 10 ml/kg, (p.o.);
3. Rats with colitis, treated with the composition of the invention, (p.o.);
4. Rats with colitis, treated with dexamethasone, (p.o) as reference.

Macroscopic and microscopic parameters were measured.

The results are summarised below and show that the composition of the invention is effective for the reduction of the inflammation and of the intestinal lesions linked to IBS and that this efficacy is lost by removing the incense from the composition.

The macroscopic parameters are the weight and faecal excretion, as reported in the table below.

It can be seen that the composition of the invention reduces the general discomfort cause by the acetic acid and the body weight remains similar to the controls.

TABLE 1

| Treatment | Body weight (g) | | Faecal excretion | |
|---|---|---|---|---|
| | Basal | Final | number | weight (g) |
| CONTROL | 213.0 ± 7.214 | 233.0 ± 6.649 | 58.38 ± 3.246 | 10.902 ± 1.778 |
| 4% ACETIC ACID | 214.0 ± 6.819 | 207.2 ± 6.180 | 10.33 ± 2.600°° | 3.167 ± 1.414°° |
| ABO/INT-10 (1 g/kg) | 212.1 ± 8.067 | 218.4 ± 9.392 | 41.00 ± 1.164** | 9.722 ± 1.007** |
| DEXAMETHASONE (1 mg/kg) | 216.1 ± 4.143 | 214.3 ± 4.177 | 40.40 ± 8.035** | 9.440 ± 1.790** |

The values represent the averages ± SEM of 8-12 animals.
Significant difference:
°°$p < 0.01$ compared to the control group;
**$p < 0.01$ compared to the group treated with acetic acid.
Where not indicated, the difference is not statistically significant.

In addition to the macroscopic data presented above, specific elements indicative of the damage to the intestine were observed and are summarised in Table 2, from which the protective effect of the product with respect to the irritative processes caused by acetic acid can be seen.

In particular, the macroscopic damage to the colon, the colon index (mg of colon/grams of rat) and the activity of myeloperoxidase, an enzyme contained in the intracellular azurophilic granules of the polymorphonuclear leukocytes (PMNs), which can therefore be used as an indicator of the accumulation of the migrated neutrophils in the tissues during an inflammatory process, are shown.

The results demonstrate strong protective activity of the composition of the invention.

TABLE 2

| Treatment | Macroscopic damage | Colon index (mg/g) | MPO (U/mg tissue) |
|---|---|---|---|
| CONTROL | 0.000 ± 0.000 | 3.868 ± 0.120 | 0.755 ± 0.078 |
| 4% ACETIC ACID | 8.833 ± 0.470°° | 8.612 ± 0.170°° | 26.070 ± 3.090°° |
| COMPOSITION OF THE INVENTION (1 g/kg) | 3.59 ± 0.438** | 6.329 ± 0.288** | 5.795 ± 0.779** |
| DEXAMETHASONE (1 mg/kg) | 4.417 ± 1.052** | 6.041 ± 0.341** | 15.387 ± 6.136** |

The values represent the averages ± SEM of 8-12 animals.
Significant difference:
°°$p < 0.01$ compared to the control group;
**$p < 0.01$ compared to the group treated with acetic acid.
Where not indicated, the difference is not statistically significant.

Myeloperoxidase is less active after 24 hours, and therefore the inflammatory activity is limited compared to the control. The composition described here, although not an anti-inflammatory like dexamethasone, demonstrates a powerful efficacy in reducing inflammation caused by external and internal agents (such as free radicals).

To verify the effectiveness of the use of the incense ingredient in the formulations, the same experiment of inflammatory colitis induced by acetic acid was carried out with a formulation devoid of incense (ABO-INT-10-2), which corresponds to the formulation Abo-INT 10 (general formulations on page 16), devoid of incense.

TABLE 3

| Treatment | Weight variation (g) | Defecations number | Defecations weight (g) |
|---|---|---|---|
| Control | 20.50 ± 1.147 | 56.67 ± 3.612 | 10.07 ± 1.984 |
| Acetic acid | −6.96 ± 1.059°° | 10.18 ± 1.381°° | 2.81 ± 0.409°° |
| ABO/INT-10-2 (1 g/kg) | 5.67 ± 0.890°° | 7.42 ± 1.716°° | 2.86 ± 0.753°° |
| Dexamethasone (1 mg/kg) | 2.167 ± 1.493°°** | 42.10 ± 9.011** | 9.44 ± 1.79** |

Table 3: The values represent the averages ± SEM of 6-12 animals.
Significant difference:
°°$p < 0.01$ compared to the control group;
*$p < 0.05$
**$p < 0.01$ compared to the group treated with acetic acid.
Where not indicated, the difference is not statistically significant.

TABLE 4

| Treatment | Macroscopic damage | Colon index (mg/g) | MPO (U/mg tissue) |
|---|---|---|---|
| Control | 0.000 ± 0.000 | 3.917 ± 0.145 | 1.065 ± 0.238 |
| 4% acetic acid | 8.409 ± 0.420°° | 9.314 ± 0.451°° | 27.013 ± 2.787°° |
| ABO/INT-10-2 (1 g/kg) | 8.292 ± 0.462°° | 8.603 ± 0.261°° | 22.633 ± 2.836°° |
| Dexamethasone (1 mg/kg) | 4.417 ± 1.052°°** | 6.041 ± 0.341°°** | 16.423 ± 5.9780°* |

The values represent the averages ± SEM of 6-12 animals.
Significant difference:
°$p < 0.05$,
°°$p < 0.01$ compared to the control group;
*$p < 0.05$ compared to the group treated with acetic acid.
Where not indicated, the difference is not statistically significant.

The effects obtained with the composition of the invention devoid of incense in the model of acute colitis induced by acetic acid are not comparable to those obtained with the reference drug dexamethasone and with the composition comprising the resins and do not demonstrate any anti-inflammatory effect, whether with regard to the macroscopic parameters (weight and faecal excretion, Table 3) or with regard to specific microscopic parameters of inflammation (Table 4).

The need for the presence of the resins as described here in the formulation for significant activity is therefore confirmed.

2. Pre-Clinical Tests of Mechanism of Action
Mucoadhesion Test

The mucoadhesion test was carried out in accordance with a model derived from the optimisation of previous experimental protocols and scientific works on the topic (D. Patel, A. W. Smith, N. Crist, P. Barnett, J. D. Smart, An in vitro mucosal model predictive of bioadhesive agents in the oral cavity, J. Controlled Release (1999) 175-183.), the mucoadhesivity of the product was determined by evaluation of the percentage of inhibition of the lectin/glycoprotein bond. CaCo2 cellular lines were used in this model to simulate the cells of the intestine.

The intestinal cells of the CaCo2 line were selected as a model of epithelial cells, since they have morphological and biochemical characteristics typical of the absorbing enterocyte present in the gastrointestinal tract and have been widely used to study the functionality of the gastrointestinal cells and also to assess the transport and/or interaction of drugs through the gastrointestinal membrane.

The cells were initially treated with biotinylated lectin (Con-A), a protein contained in some leguminosae (*Canavalia ensiformis*) having a high infinity for the glucoside and mannoside residues present in the glycoproteins of the membrane. The sites of the glycoproteins of the mucosal membranes are thus occupied with the biotinylated lectin. The presence of the biotin (vitamin H) in the lectin is indispensable for the next stage. The cells already treated with biotinylated lectin are in fact charged with streptavidin peroxidase, making it possible to form the protein/glucose/lectin/biotin/streptavidin peroxidase complex due to the high affinity between biotin and streptavidin.

At this point, the cells were washed and the protein/glucose/lectin/biotin/streptavidin peroxidase complex was quantified, thanks to the presence of the peroxidase, by means of a reaction of oxidation of the ortho-phenylenediamine.

In fact, the protein/glucose/lectin/biotin/streptavidin peroxidase complex catalyses the polymerisation reaction:

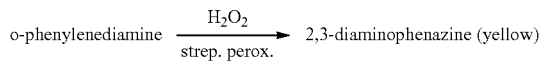

The intensity of the yellow/orange colouration of the solution (measured using a spectrophotometer with λ=450 nm) is proportional to the quantity of glycoprotein/lectin bonds and therefore to the quantity of available sites (glycoproteins) for mucoadhesion.

The absorbency value thus determined constitutes the "control".

When determining the mucoadhesivity of the product, in accordance with the general formula on page 16, the mucosal cells are treated preliminarily with this product by means of incubation at 30° C. for 15 minutes before the treatment with lectin. The mucoadhesive substances contained in the product under examination are thus able to bond to the glucoside and mannoside sites present in the glycoproteins of the mucosal membranes.

In the next phase, adding the sequence of biotinylated lectin, streptavidin peroxidase and ortho-phenylenediamine, it is possible to obtain a less intense colouration compared to the control (obtained without pre-treatment with the product to be tested), since some of the glucoside sites available for bonding with the Con-A were already occupied by the mucoadhesive substances present in the product. In fact, the initial bonding between the mucoadhesive substances contained in the product to be tested and the glucoside sites partly compromises the subsequent conjugation of the Con-A with the streptavidin peroxidase complex and the subsequent development of colour after addition of oxygenated water.

The decrease in the absorbency value is in fact proportional to the ability of the substances under examination to "mucoadhere" to the CaCo2 cells.

The mucoadhesive ability is expressed as a percentage of inhibition of glycoprotein/lectin bonding and represents the percentage of mucosal sites occupied by the product compared to those captured by the lectins in the control test. This parameter can also be defined as "percentage of mucoadhesion of the product" in accordance with the following equation:

Percentage of mucoadhesion of the product=(1 abs sample/abs control)×100

Furthermore, in addition to the mucoadhesive ability, an essential requirement of a product intended for protective treatment of a mucosal surface is the resistance of the layer of mucoadhesion (formed by interaction of the product with the mucosal cells) to the action of the solution with which it comes into contact and, in the case of nasal treatment, with mucus.

To this end, in a second phase of the experiment, the resistance over time (0.5-2 h) of the mucoadhesivity produced by the formulation after treatment of the mucosal cells was evaluated. For this determination, the mucosal cells treated with the formulation under examination were subjected to a continuous flow of an isotonic solution containing 2% mucin, able to mimic the mucosal fluid present in the nose.

To execute this second protocol, a system of Franz cells was utilised, these cells generally being used in the assessment of the process of percutaneous absorption of a substance or for the study of other processes of permeation through natural or artificial membranes.

Materials and Methods

The composition of the invention as provided by way of example in the general formula on page 16 (the compositions on page 16 and composition example 1 were tested in parallel and gave comparable results) was diluted 1:2 and 1:5 in physiological saline solution (NaCl 0.9%) containing phosphate buffer (pH 6.8). The suspension was subjected to sonication and the solution obtained was filtered conveniently. The CaCo-2 cells were kept in MEM with the addition of 10% of foetal bovine serum, 100 U/ml of penicillin and 100 μg/ml of streptomycin and held at 37° C. in an incubator under humidified atmosphere formed of 95% air and 5% CO2. The culture medium was changed every 2-3 days. 24 hours before the experiment, the cells were trypsinized, counted in a haemocytometer, centrifuged and resuspended in TBS. The cellular suspension was then divided into 2 test tubes: in the first test tube, only the vehicle was added; in the second test tube, 5 ml of the solution containing the granulate at suitable dilution were added. The 2 test tubes were left under stirring at 30° C. for 15 minutes. The cells were then washed 3 times in TBS. 5 ml of TBS 0.05M containing CaCl2 1mM and biotinylated lectin were then added to both test tubes over a period of 30 minutes at 30° C. with gentle stirring. After 3 washes, the cellular suspension was incubated with 5 ml of TBS 0.125M containing streptavidin peroxidase and left to incubate for 60 minutes at 30° C. with gentle stirring. The cells were then washed 3 times and lastly resuspended in 1 ml of solution of o-pd (containing 0.4 mg of o-pd in citrate buffer and 0.4 μl of H2O2). The oxidation of the o-pd produced a yellow colouration and the reaction was stopped after 1 minute by the addition of HCl 1N. The optical density was measured at 492 nm by means of spectrophotometric reading. The experiment was carried out three times.

Experimental Protocols

Evaluation of Retention of the Mucoadhesivity

For this experiment, a system formed of six Franz cells was used. Franz cells are used widely in the literature in order to study the process of absorption of a compound through the skin or other membranes (artificial or biological).

In percutaneous absorption studies, a membrane formed by full skin (epidermis/dermis) or by stratum corneum/epidermis (SCE) membrane, obtained almost always by reductive cosmetic surgery, is placed between these two chambers. The formulation containing the product as described on page 16, general formula (tested among the examples on page 16 and the composition examples stated thereafter, which have given results comparable among one another), the cutaneous permeation process of which is to be evaluated, is therefore placed in the donor whilst the receptor is filled with a physiological solution. The temperature of the receptor is controlled by circulation of water in an outer jacket, and the samples of the receptor solution, in which the quantities of substance penetrated over time through the skin will be determined, are taken from the lateral arm using a long stem syringe.

In the experiment carried out in order to evaluate the retention of the mucoadhesivity of the composition of the invention, cellular CaCo-2 cultures, treated with the product ABO/INT-10 (also referred to as ABO-INT or example composition 1), diluted 1:5, were placed in the donor.

The main objective of this study was to evaluate the mucoadhesion in vitro of the composition of the invention. The results obtained in this experiment show that the formulation of the invention has an interesting mucoadhesive ability with respect to CaCo-2 mucosal cells, used as a model of gastrointestinal mucosal cells.

In addition, the evaluation of resistance to the solution simulating the intestinal juice of the mucoadhesive and protective layer formed following treatment of the mucosal cells with the formulation of the invention (diluted 1:5) demonstrates a good capacity of retention of the mucoadhesivity, particularly in the first hour, but also beyond, subsequently to the application of the diluted product to the cells.

In light of the results obtained, it is possible to confirm that the product, demonstrating good, resistant mucoadhesivity to the gastrointestinal mucosal cells, can play an efficient protective role on the mucosa of the gastrointestinal tract.

TABLE 5

| Tests carried out | Result | Laboratory report no. |
| --- | --- | --- |
| Mucoadhesion test | The composition of the invention has affinity to and bonds to the intestinal mucosal sites at a rate of 68% and 52% at dilutions of 1:2 and 1:5 respectively This adhesion is maintained over time | In vitro test on CaCo-2 cells |

Figure 2:
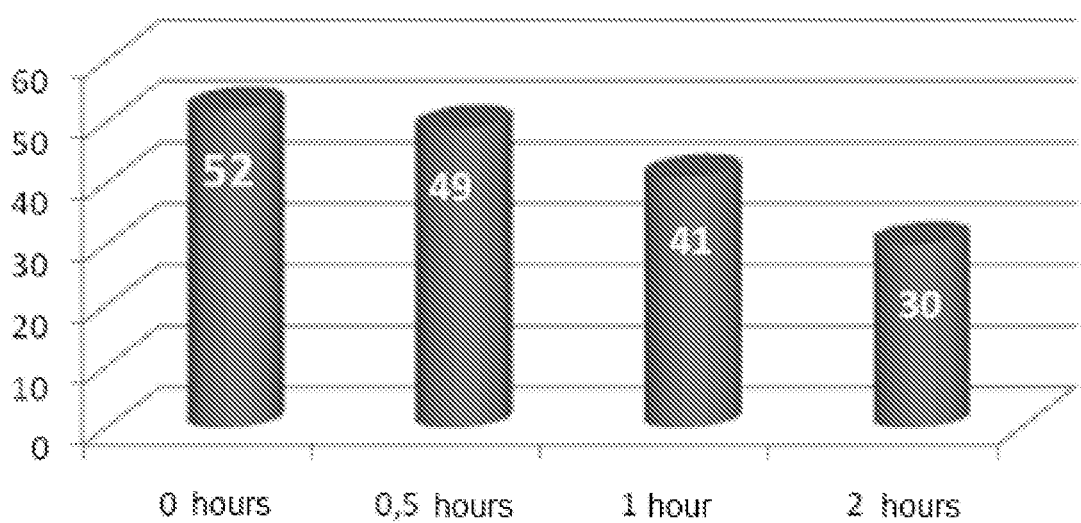

The results of the mucoadhesion tests are also shown in FIGS. 1 and 2, where the mucoadhesivity of the composition (FIG. 1) and the resistance of the composition to simulated washing with gastric juices (FIG. 2) are illustrated.

3 In vitro Assessment of the Protective Effect of the Composition of the Invention Following Information Caused by LPS The composition of the invention has demonstrated protective activity on a primary line of human fibroblasts (HuDe), that is to say it has demonstrated indirect anti-inflammatory properties, from inflammation caused by LPS, which is a known sensitising and inflammatory substance.

Three different types of experiments were carried out.

cells exposed to LPS treatment and monitored in order to determine the cytokines produced after 24 hours; (negative control)

cells exposed to LPS treatment and, after 30 minutes, supplemented by the product of the invention (two concentrations) and then monitored in order to determine the cytokines produced after 24 hours (protective post-exposure activity);

cells supplemented by the product of the invention (two concentrations), supplemented after 30 minutes by LPS and then monitored in order to determine the cytokines produced after 24 hours (preventative protective activity).

The protective power was verified by measuring the IL8 secreted by the HuDe after exposure.

TABLE 6

| | % of inhibition of IL-8 | |
| --- | --- | --- |
| | Pre-treatment with ABO/INT | Post-treatment with ABO/INT |
| Conc. 10 μg/ml | 62.4 ± 5.8 | 32.6 ± 4.5 |
| Conc. 100 μg/ml | 82.2 ± 6.1 | 45.8 ± 7.2 |

The table clearly shows how the effect of reducing inflammation appears to be implemented by the composition described here by means of a protective barrier mechanism. The pre-treatment is clearly greater than the post-treatment. The anti-inflammatory effect observed in the post-treatment is probably still caused by the protective effect, which acts less efficiently since the harmful agent has already been able to come into contact with the mucosa.

The data correspond to the results obtained with the mucoadhesion test in that greater concentrations give improved effects, but not fundamentally different effects.

To confirm the contribution of the incense ingredient, rich in resins, to the local protective action, the aforementioned test of the barrier effect was repeated with the formulation of the invention as described on page 16 and in the examples and in a formulation devoid of incense (ABO/INT-10-2) and was assessed at a concentration of 100 μg/ml for protection with respect to the production of interleukin 6, induced by LPS.

TABLE 7

| SAMPLE | % of inhibition of IL-6 release |
| --- | --- |
| ABO/INT-10 | 95% |
| ABO/INT-10-2 | 65% |

The results indicate that the incense contributes to an increase in the barrier effect from 65% of inhibition of IL-6 release (formulation without incense) to 95% (formulation with incense).

This last test also indicates the further protection of the formulation toward the production of IL-6 and not just IL-8.

4. Antioxidant Activity Test

In order to verify the antioxidant power of the composition of the invention in a biological system similar to the intestinal epithelium (CaCo-2), the following tests were carried out:

Evaluation of the antioxidant activity of the sample on human cells subject to chemical, progressive oxidative stress. The assessment of the antioxidant action is acquired from the quantification of the formation of free radicals in cells exposed to the sample and to oxidative stress. The antioxidant activity of the sample in analyses was evaluated by comparison with that of a safe hydrosoluble antioxidant, such as vitamin C.

Cellular vitality test: Neutral Red Uptake (NRU).

At the end of the antioxidant activity test, the cellular vitality test MTT was carried out in order to verify that the decrease in the formation of free radicals was caused by actual efficacy and not by a cytotoxic effect of the product under examination.

The protocol is based on the use of a fluorescent probe called 2',7'-dichlorofluorescein diacetate (DCFH-DA), a non-fluorescent stable molecule that enters the cells, bonds to the membrane macromolecules, where it is hydrolysed from cytoplasmic esterases to give dichlorofluorescein (DCFH), a molecule that again is non-fluorescent. DCFH, in the presence of free radicals, is oxidised, forming a highly fluorescent molecule: DCF.

The oxidative stress is induced via oxygenated water.

The radicals produced constitutively from the cells with the addition of the sample, but without the addition of the oxidising agent, were also monitored as a negative control (absence of oxidant activity of the composition of the invention).

Figure 3:
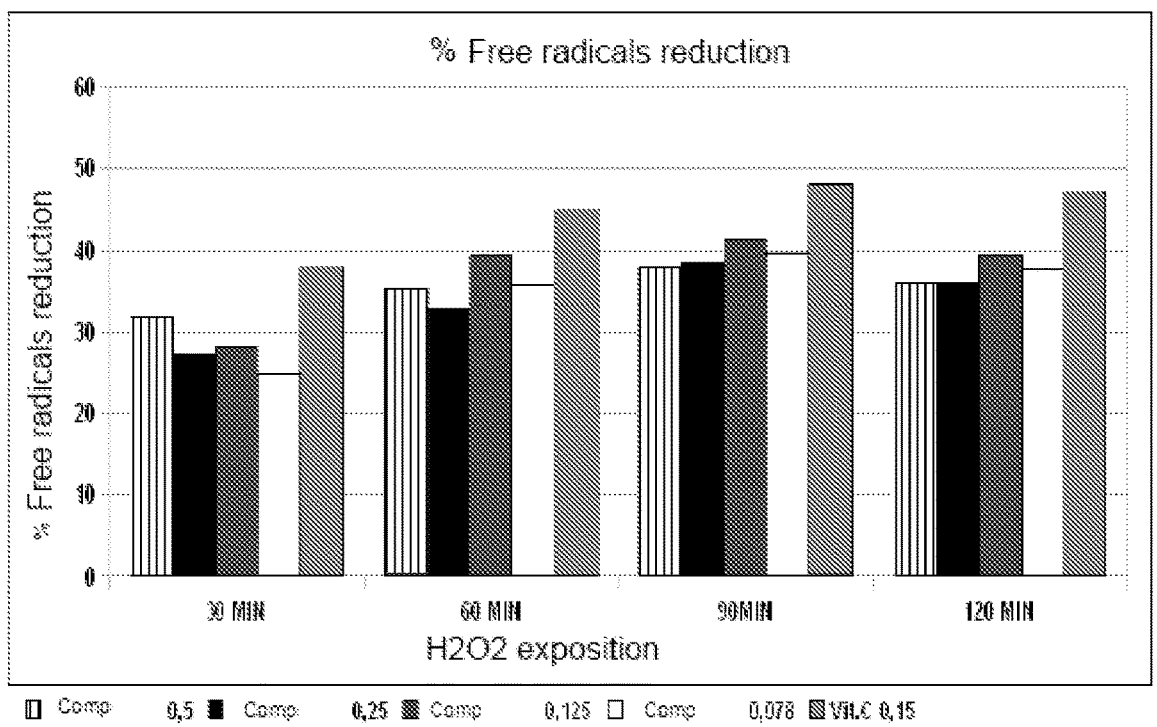

As shown in FIG. 3, the composition demonstrated good scavenger activity of the free radicals, comparable to that demonstrated by vitamin C. In addition, the product does not promote the production of free radicals and therefore does not have an oxidant effect per se.

The composition has been found to be an optimum scavenger: its presence guarantees optimum neutralising action of the free radicals originating from the endogenous metabolism comparable to that of vitamin C and good buffering action, even in the presence of significant environmental and behavioural stresses. This action could contribute significantly not just to the maintenance of the state of wellbeing of the intestinal epithelium, but could be an optimum adjuvant for reestablishment of this state in individuals suffering from irritable bowel syndrome.

5. Toxicity

As experimental confirmation of the safety observed in the literature, the biocompatibility test was carried out on the composition of the invention in accordance with ISO-10993, and the safety of the product was confirmed, since, beyond the safety known from the literature, the tests reveal a product:

that does not irritate the intestinal mucosa,
that is not sensitising,
that is not cytotoxic
that is not toxic by acute oral administration at concentrations >2000 mg/kg.

6. Clinical Experience Gathered from Informed Patients Affected by IBS

With the collaboration of medical specialists, case studies were collected on patients affected by irritable bowel syndrome and to whom the composition of the invention was administered in accordance with the guidance and medical practice of the collaborating doctors for individuals taking part in their study and affected by irritable bowel syndrome.

Without interfering with medical practice, but requesting the collaboration of the patient with regard to the diligence of the therapy, the patients were requested to fill in the validated questionnaires (Francis, 1997) in order to assess their response to the product in addition to authorisation to process the data.

The case studies reported concern 6 weeks of treatment in accordance with the following indications: 6 cp per day, divided into 2 cp 1 hour before breakfast, 2 cp 1 hour before lunch and 2 cp 1 hour before dinner. After the first visit, two check-up visits were carried out after 3 and 6 weeks. 44 patients took part in the study, of which 6 did not complete the period of treatment.

These were carried out with compositions as described above:

Total daily does between 2000 and 3000 mg of the composition as described in the detailed part of the invention comprising lyophilised resin incense extract, dehydrated Aloe vera leaf gel, lyophilised camomile flower extract and lemon-balm, plus adjuvants q.s. to 2000-3000 mg.

6.1 Methods for Evaluating the Clinical Effects of the Composition of the Invention The variations of the gastrointestinal symptomatology following administration of the composition were examined in two ways:

1) by means of a daily journal that was compiled by the patients both during the day before treatment was started and afterwards for the entire duration of the study with regard to abdominal pain and bloating, scored using an ordinal scale from 1-5 points, and with regard to the bowel, reporting the number of daily excretions. The patients were also asked to evaluate, on a day-by-day basis, the degree of wellbeing with regard to the gastrointestinal system at the end of each day using a score from 1 to 5.

This method makes it possible to follow the development of the symptomatology step-by-step throughout the course of treatment and was considered rather suitable for this type of evaluation by significant international journals concerning internal medicine and gastroenterology during prior works concerning the therapy of gastrointestinal functional disorders (New England Journal of Medicine, Gastroenterology, Alimentary Pharmacology and Therapeutics)

2) by means of the Francis questionnaire (Francis C Y, Morris J, Whorwell P J. The irritable bowel severity score system: a simple method of monitoring irritable bowel syndrome and its progress. Aliment Pharmacol Ther 1997; 11:395-402), which was filled in 3 times: before treatment was started, after an interval of approximately three weeks, and at the end of treatment after 6 weeks, and by means of the IBS 36 questionnaire on the quality of life, filled in at the start and end of treatment.

All patients were also asked to give a subjective opinion at the final visit (V3) on the efficacy of the therapy, on any improvement in the quality of life, on the difficulty in taking the product and on the appearance of side effects, and lastly to state their desire to proceed or not with the therapy just concluded.

The Francis and quality of life questionnaires filled in during this study were subject to statistical evaluation.

Evaluation by Means of Daily Journal

The observations were carried out on 20 patients affected by irritable bowel syndrome to whom the product as described in the general formula on page 16 was administered in an open and non-controlled manner, evaluating the symptomatology before and after administration by means of the compilation of a daily diary with final evaluation by the patient.

The patients examined for the case studies were patients without physical or mental complications and with no other relevant pathologies, and were not under antibiotic therapy or had not just started a new therapy.

Evaluation of the symptoms

The patients compiled a daily or weekly journal from the day before treatment was started and thereafter for the entire duration of the study:

evaluating the abdominal pain and distension by means of a 5-point ordinal scale, in which:

1=no symptom, 2=mild symptom, 3=symptom of average intensity, 4=strong symptom, 5=very strong symptom and reporting the number of daily excretions.

The patients were also asked to evaluate on a day-by-day basis the level of gastrointestinal wellbeing at the end of each day using a score from 1 to 5 (1 =terrible, 5=excellent); and, at the final visit (V6) to give a final opinion on the efficacy of the treatment, on any improvement in the quality of life, on the difficulty in taking the product and on the appearance of side effects, and also on the availability to repeat the treatment.

Statistical Analysis

The average weekly scores for each parameter were calculated and compared to the values of the base period using the Students t-test for paired data.

Results

Of the 44 patients analysed, 16 compiled the journals.

Figure 5:
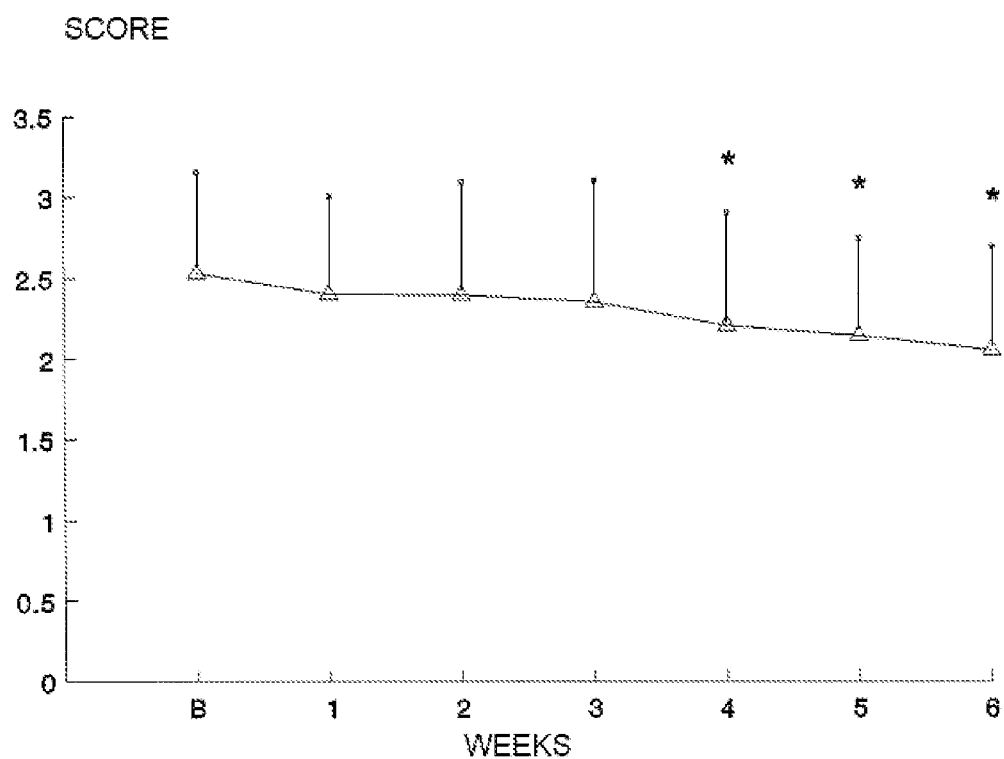
Figure 6:
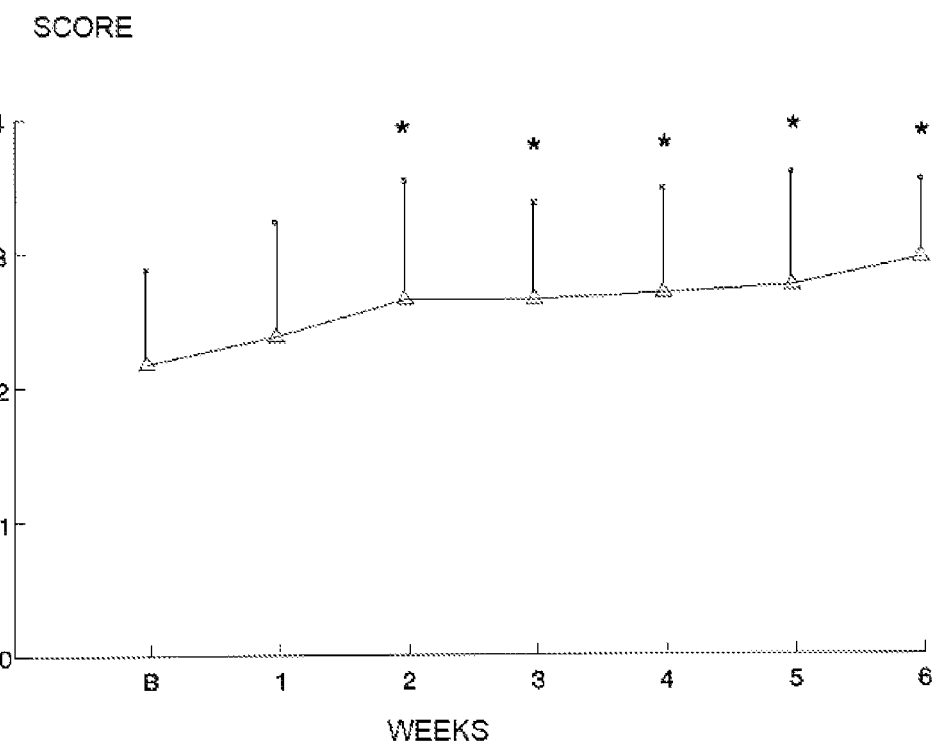

The analysis of the results demonstrated that both abdominal pain and abdominal bloating are significantly reduced compared to the base control period from the fourth week of treatment until the end of treatment (FIGS. 5 and 6).

Figure 4:
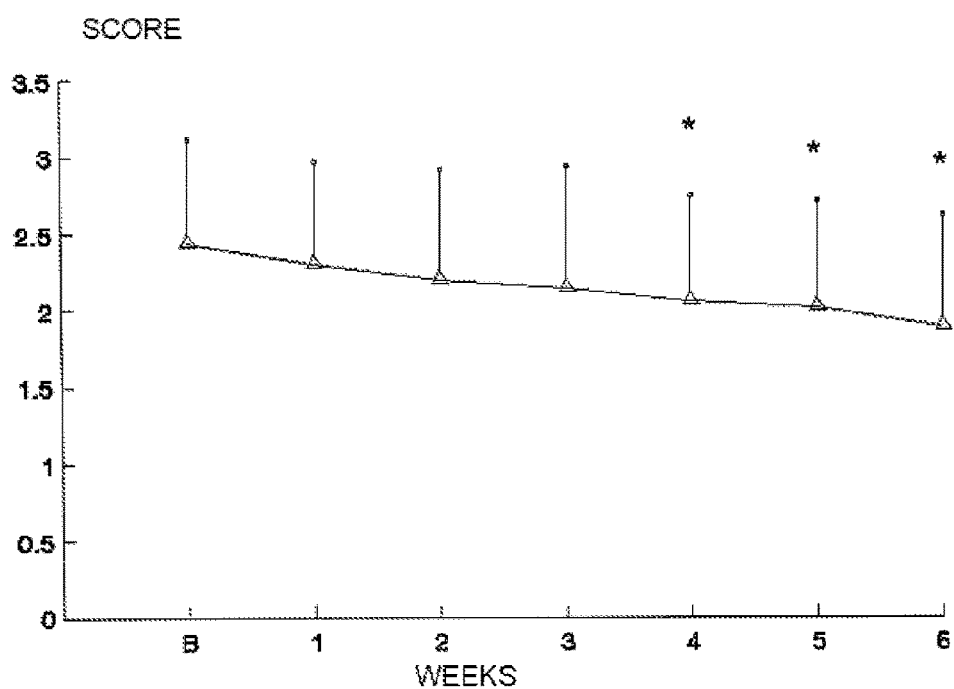

The daily subjective evaluation of the state of gastrointestinal wellbeing is significantly improved compared to the base control period from the second week until the sixth week (FIG. 4).

The effect on the number of defecations is insignificant. In fact, the number of defecations passed from 1.86±1.14 (average ±SD) during the base period to 2±1.09 after 3 weeks and to 1.78±1.13 after 6 weeks.

Since the number of patients treated was low, it was not possible to establish with certainty whether there are differences between the various types of irritable bowel syndrome with constipation, with diarrhoea, and mixed.

Figure 7:
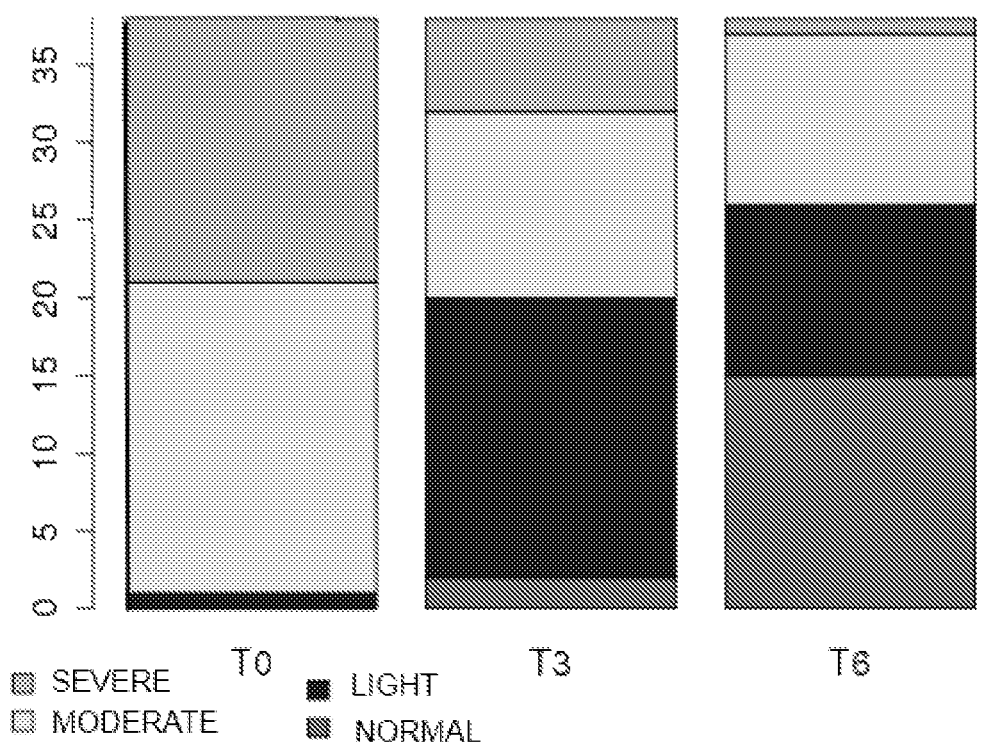
Figure 8:
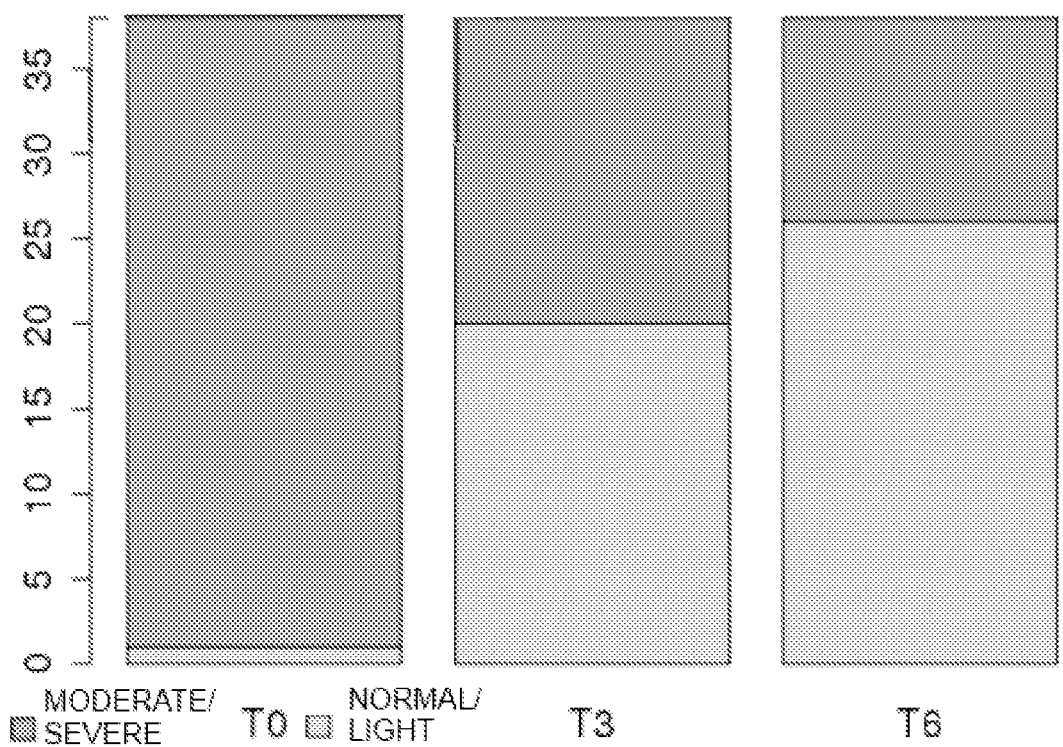
FIG. 8 shows the same results with aggregation of the classes "severe" and "moderate" and of the classes "mild" and "normal" (number of individuals on the ordinate and time expressed in weeks on the abscissa).
Figure 9:
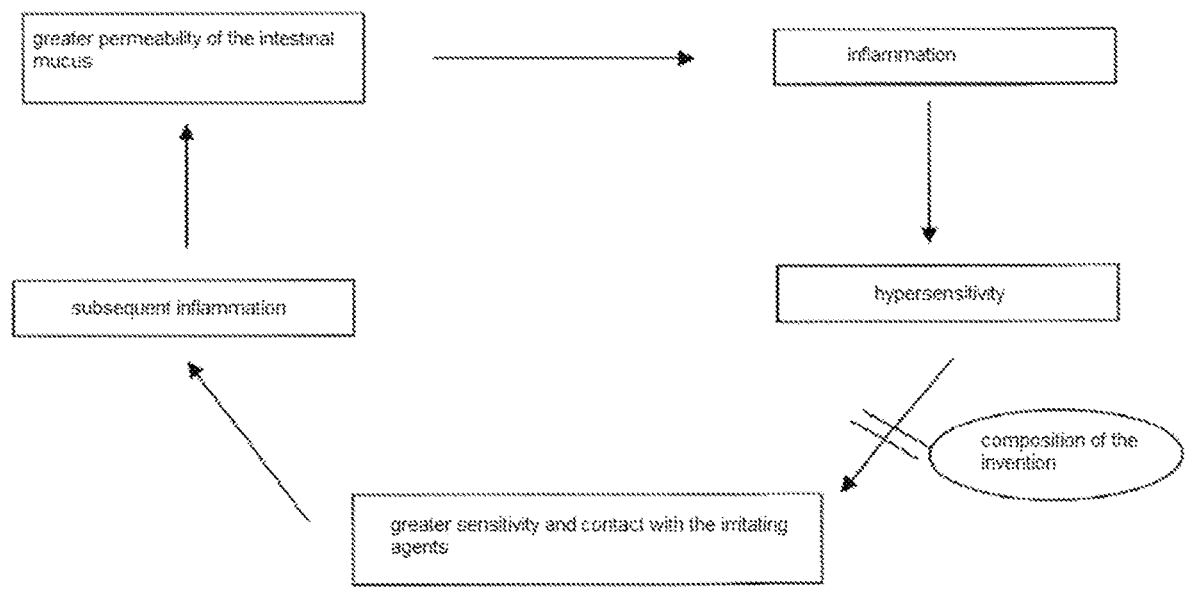
FIG. 9 shows that without being bound to theory, it is hypothesized that the composition according to the invention can act in accordance with the schema, blocking the vicious circle.
Figure 10:
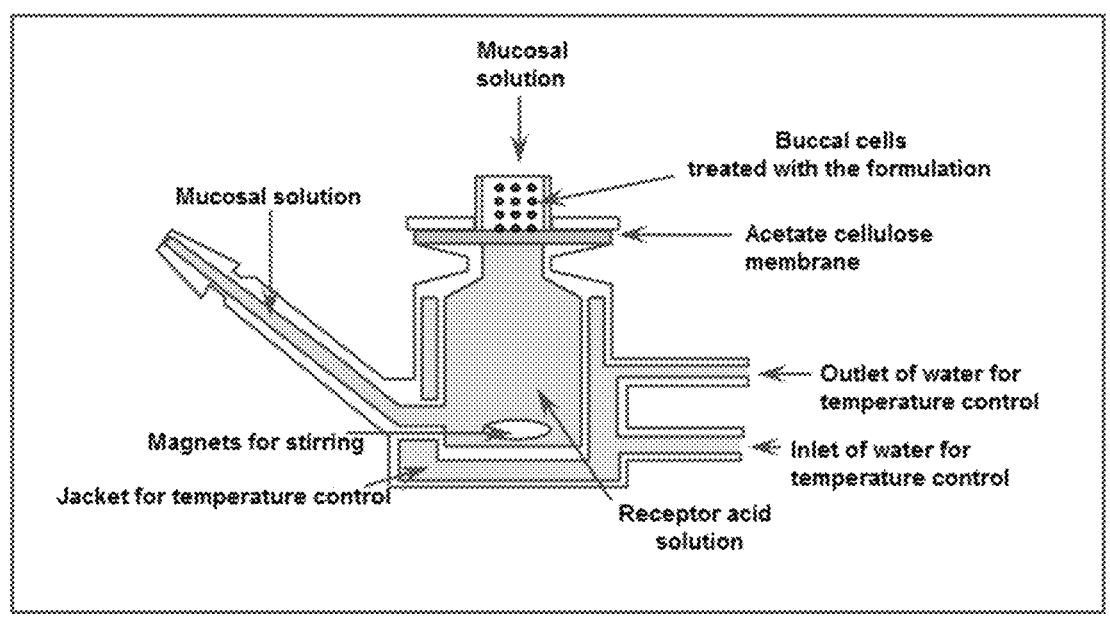
FIG. 10 shows the Franz cell is formed by a donor and by a receptor. Franz cell is used to determine the resistance of the mucoadhesive layer (formed by the application of the formulation to the mucosal cells) subjected to a flow of a mucin solution, simulating the mucosal solution present in the nose.

Evaluation by Means of Francis Questionnaire and IBS-36 Quality of Life Questionnaire The patients were the same patients who had completed the journal, plus others selected in accordance with the same criteria described above, that is to say affected by IBS without further complications. The Francis study has shown that abdominal pain is significantly reduced (evaluated by means of Pearson's chi-squared test) both after 3 weeks (−36.7%) and after 6 weeks (−60.3%). In fact, the population moved gradually from scores corresponding to moderate or severe discomfort (97% at the start compared to 32% after 6 weeks) to scores indicating no discomfort or minimal discomfort (3% at the start compared to 68% after 6 weeks). These data are shown in FIGS. 7 and 8, in which the variations of the symptoms relating to abdominal pain and discomfort linked to IBS are illustrated over time (T0, T3 and T6, which respectively represent the start, 3 weeks, and 6 weeks of therapy) for symptomatology with "severe", "average", "mild" and "normal" intensity in FIG. 7 and "severe +average" and "mild +normal" in FIG. 8.

The definitions of severe, average, mild and normal were appointed in accordance with the 1997 Francis questionnaire indicated above.

In addition, the IBS-specific symptoms, such as discomfort linked to defecation and characteristics of the stools, also passed from "moderate or severe" intensity to "mild" intensity. The stools became more "normal" and in particular became less "hard" with a reduction in the "urgency" for excretion.

There is no significant variation with regard to lost working weeks and weeks with pain in the workplace.

The patients demonstrate good acceptance of the product, which they judged to be extremely or very effective in 57.9% of cases with significant improvement in the quality of life in 57.9% of cases and no experience of discomfort or intolerance in 91.2% of cases.

90% of patients wanted to continue taking the product.

With regard to the scoring observed in the questionnaire on the quality of life developed specifically for IBS, the results were rather positive. In fact, the overall score of the questionnaire fell statistically significantly over the 6 weeks of treatment, demonstrating an improvement in the quality of life.

Mucoadhesivity Test of the Composition of the Invention and of its Protective Effect on the Intestinal Mucosa with Respect to Damage Induced by Hydrochloride in an Ussing Chamber The experiment was conducted in order to verify the effects of the tested substances on the artificially damaged intestinal mucosa ex vivo (for example hydrochloric acid).

40 male Sprague Dawley rats weighing approximately 200-250 g were used for the test.

The rats were housed in cages measuring 160×270×440 mm (height, width, length) under controlled temperature and humidity and a light/dark cycle with variation every 12 hours.

The cages were cleaned and disinfected before use, the animals were given a standard diet with pellets, and purified water was distributed ad libitum.

Krebs buffer was used as a reagent: 115 mM NaCl from VWR International Ltd (BDH), 8 mM KCl, 1.25 mM CaCl2, 1.2 mM MgSO4(7H20), 2 mM NaH2PO4, 5.5 mM D-glucose and 225 mM NaHCO3 from Merck. The pH of the solution was controlled using 1.0 N HCl or using 1.0 N NaOH from Merck, the pH was measured using an electrode (Radiometer Copenhagen PHM82 Standard pH Meter).

The Ussing Chamber system EVC-4000 was from World Precision Instrument Inc.

The anaesthetic solution contained 10% Imalgene 1000 (ketamine hydrochloride 100 mg/ml) and 2.5% Rompun (xylazine hydrochloride 23.32 mg), both from Bayer.

Rational and Treatment 4 groups of 8 rats A, B, C, D were formed, respectively containing untreated rats, rats treated with 1.0 ml saline solution intragastrically, rats treated with 1.0 ml (500 mg/kg of body weight) of composition of the invention intragastrically, and rats treated with 1.0 ml of dexamethasone (1 mg/kg of body weight) intragastrically.

The untreated group was not isolated in order to avoid damage to the mucosa linked to stress, whereas in the other cases the animals were isolated in order to evaluate the damage to the mucosa, avoiding the variable "food".

The animals in groups A, B, C and D were deprived of food for 18 hours.

Four rats per group were anaesthetised 30 minutes after the above-indicated administration by means of intraperitoneal injection and were kept in a heated atmosphere.

A sample of the duodenum was then dissected from these rats and mounted between the two half-chambers of the Ussing chamber and damage was induced using hydrochloride (pH 8.0; pH 5.5).

Four rats per group were then anaesthetised 50 minutes after the above-indicated administration by means of intraperitoneal injection and were kept in a heated atmosphere.

A sample of the ileum was then dissected from these rats and mounted between the two half-chambers of the Ussing chamber and damage was induced using hydrochloride (pH 8.0; pH 6.5).

The pH values for the damage were selected in accordance with tests carried out for the evaluation of mucosal damage since the physiological pH of the duodenum is approximately 7.35 in the duodenum and approximately 8 in the ileum, the transit time of the composition of the invention was checked beforehand and reached the duodenum approximately 30 minutes after administration and reached the ileum approximately 50 minutes after administration.

Preparation of the Tissue

The duodenum or ileum was removed from the anaesthetised animals by means of abdominal incision in anaesthetised animals and was immediately placed in Krebs buffer having the respective optimal pH values indicated above, the buffer being pre-heated and oxygenated. A sample of approximately 0.25 cm$^2$ was then taken.

The sampled segments were assembled in the two half-chambers of the Ussing system (opening 0.125 cm$^2$). Two voltage-sensitive electrodes and two Ag-AgCl electrodes passing current to the Ussing chamber via agar bridges were connected.

The chamber thus assembled was placed in a block containing a bath of water circulating at 28° C. and the half-chambers were filled with oxygenated Krebs buffer from either sides of the tissue.

The mucosal and serous sides of the chamber were both connected to sterile tanks containing 10 ml of oxygenated Krebs buffer and were kept at 28° and subjected to a gas flow containing 95% oxygen and 5% carbonic anhydride.

5.5 mM D-glucose was added on both sides.

Once the intestinal membrane was assembled in the Ussing chamber, the system was stabilised for 10 minutes in order to test the function thereof and the integrity of the intestinal membranes.

The ddp in mV through the mucosal membrane was measured directly as well as the short-circuit current, and these were monitored for 15 minutes whilst the transmembrane resistance was calculated in ohm x cm$^2$ using Ohm's law.

The tanks were then emptied and then refilled with Krebs buffer having a pH of 5.5 for the duodenum and a pH of 6.5 for the ileum.

The system was then stabilised for 10 minutes and the same parameters as indicated above were then measured for 15 minutes.

The pH was controlled as described above.

Since hydrochloric acid causes mechanical damage to the integrity of the mucosa, the maintenance of mucosal integrity in acid conditions is directly proportional to the mechanical protective effect of the tested product ("mechanical" means an effect that is not pharmacological, immunological or metabolic).

The data are reported as an average ±SD. The comparison was made using the students t-test and the significance was *p<0.05; p<0.01; *p<0.001.

The groups were compared as follows:

Control group B was analysed in relation to the unstressed group A in order to verify whether stress alone was responsible for damage or for greater sensitivity to the induced damage of the mucosa.

Groups C and D were compared with group B to verify whether the administered product was protective or not of the mucosa in the stressed rats and with induced damage compared to the control group, which was merely stressed.

RESULTS

Group A (Untreated, Fed and Not Isolated—NO STRESS)

The experiment described above in the Ussing chamber was carried out in order to evaluate the resistance of the intestinal mucosa of untreated rats, without isolation, using the above protocol.

The results obtained show that the average value of resistance of the duodenum in physiological conditions with Krebs buffer at the above-indicated physiological pH was 87.0±23.9 ohm×cm$^2$.

After induction of damage with Krebs buffer at pH 5.5, the resistance demonstrated an average value of 71.4±20.7 ohm×cm$^2$.

The average value of resistance of the ileum in physiological conditions with Krebs buffer at the above-indicated physiological pH was 68.1±20.9 ohm×cm$^2$.

After induction of damage with Krebs buffer at pH 6.5, the resistance demonstrated an average value of 58.7±22.7 ohm×cm$^2$.

Maximum protection is therefore at physiological pH, and the untreated mucosa seems also to have a potential for protection probably caused by food and by the protective mucus present in the unstressed mucosa.

Group B (Isolated Rats—STRESS—Treated Only Physiologically, Control)

Carrying out the experiment described above in the Ussing chamber, the results obtained show that:

The average value of resistance of the duodenum in physiological conditions with Krebs buffer at the above-indicated physiological pH was 73.0±8.7 ohm×cm$^2$.

After induction of damage with Krebs buffer at pH 5.5, the resistance demonstrated an average value of 62.0±8.8 ohm×cm$^2$.

The average value of resistance of the ileum in physiological conditions with Krebs buffer at the above-indicated physiological pH was 51.5±4.3 ohm×cm$^2$.

After induction of the damage with Krebs buffer at pH 6.5, the resistance demonstrated an average value of 44.9±4.7 ohm×cm$^2$.

These data therefore show that the presence of stress alone, a factor which is also present in IBS, is sufficient to considerably reduce the natural protection presented by a healthy intestinal mucosa (values before treatment at acidic pH) and that the resistance of the mucosa reduces by a good 9 points in the duodenum and by 7 points in the ileum following treatment with acid with a statistical significance, compared to group A (unstressed) of p<0.01 for the values observed in the duodenum and of *p<0.001 for the values observed in the ileum after induction of the damage.

Group C (Isolated Rats—STRESS—Treated with the Composition According to the Invention)

Carrying out the above-described experiment in the Ussing chamber, the results obtained, reported for the compound according to composition 1 and comparable with the data obtained with the other exemplary compositions, show that:

The average value of resistance of the duodenum in physiological conditions with Krebs buffer at the above-indicated physiological pH was 79.1±6.9 ohm×cm$^2$.

After induction of damage with Krebs buffer at pH 5.5, the resistance demonstrated an average value of 69.0±4.1 ohm×cm$^2$.

The average value of resistance of the ileum in physiological conditions with Krebs buffer at the above-indicated physiological pH was 51.4±7.9 ohm×cm$^2$.

After induction of the damage with Krebs buffer at pH 6.5, the resistance demonstrated an average value of 46.1±7.7 ohm×cm$^2$, which indicates that the physiological barrier activity of the tissue was preserved.

This group demonstrates a pre-damage resistance in line with the control group B, the duodenal resistance is significantly greater in this group compared to the control group B ***p<0.001, whilst the greater resistance observed in the ileum is not statistically significant however.

Group D (Isolated Rats—STRESS—Treated with Dexamethasone)

Carrying out the above-described experiment in the Ussing chamber, the results obtained show that:

The average value of resistance of the duodenum in physiological conditions with Krebs buffer at the above-indicated physiological pH was 50.4±13.9 ohm×cm$^2$.

After induction of damage with Krebs buffer at pH 5.5, the resistance demonstrated an average value of 48.0±12.7 ohm×cm$^2$.

The average value of resistance of the ileum in physiological conditions with Krebs buffer at the above-indicated physiological pH was 50.6±13.4 ohm×cm$^2$.

After induction of the damage with Krebs buffer at pH 6.5, the resistance demonstrated an average value of 39.7±8.1 ohm×cm$^2$, which indicates that the physiological barrier activity of the tissue was reduced.

The group with dexamethasone demonstrated reduced duodenal integrity, even at physiological pH, probably due to the gastric damage caused by the cortisones, however mucosal integrity was not drastically reduced after the treatment with acid since the mucosa was already very damaged.

The invention claimed is:

1. A composition for treatment of a patient suffering from irritable bowel syndrome (IBS), which protects the patient's intestinal mucosa by producing a barrier effect thereon and increasing adhesivity of said barrier to the patient's intestinal mucosa, comprising: (a) resin incense extract in a weight percentage from 20% to 60%, (b) one or more polysaccharides and/or plant extracts comprising polysaccharides in a weight percentage from 12% to 22%, and (c) one or more antioxidants and/or plant extracts comprising antioxidants in a weight percentage from 35% to 65%; wherein said polysaccharides are selected from the group consisting of polysaccharides extracted from Aloe vera, polysaccharides extracted from chamomile, and polysaccharides extracted from althea; wherein said plant extracts comprising polysaccharides are selected from the group consisting of extracts of Aloe vera, extracts of chamomile, and extracts of althea; wherein said antioxidants are selected from the group consisting of antioxidants extracted from chamomile and antioxidants extracted from lemon-balm; and wherein said plant extracts comprising antioxidants are selected from the group consisting of extracts of chamomile and extracts of lemon-balm.

2. The composition according to claim 1 further comprising one or more natural and/or plant derived compounds selected from the group consisting of gentian root extract, boldo leaf extract, milk thistle fruit extract, artichoke leaves extract, dandelion root extract, anise fruit extract, rosemary leaf extract, mint leaf extract, marjoram leaf extract, cumin fruit extract, cumin seed extract, coriander fruit extract, ginger root extract, fennel fruit extract, caraway fruit extract, plant charcoal, and inulin.

3. The composition according to claim 1 in a form suitable for oral administration.

4. The composition according to claim 1 wherein said composition is a pharmaceutical composition, is comprised in a medical device, is comprised in a dietary supplement, or is comprised in a medical food.

5. A medical device, medicament, medical food, or dietary supplement comprising a composition according to claim 1.

6. A method for preparation of a composition according to claim 1, comprising admixing together one or more of said resin incense extract, one or more of said polysaccharides and/or plant extracts comprising polysaccharides, and one or more of said antioxidants and/or plant extracts comprising antioxidants; together with further excipients.

7. A method for treatment of a patient suffering from irritable bowel syndrome (IBS), comprising administering a composition according to claim 1 to a patient in need thereof.

8. A method for preparation of a composition according to claim 1, comprising admixing together one or more of said resin incense extract, one or more of said polysaccharides and/or plant extracts comprising polysaccharides, and one or more of said antioxidants and/or plant extracts comprising antioxidants; together with further excipients and/or one or more of said natural and/or plant derived compounds having activity suitable for relieving effects of IBS.

9. The composition according to claim 1 wherein said resin incense extract is in a percentage from 20% to 30% by weight.

10. The composition according to claim 1 wherein said polysaccharides and/or plant extracts comprising polysaccharides are in a percentage from 7% to 13% by weight.

11. The composition according to claim 1 wherein said antioxidants and/or plant extracts comprising antioxidants are in a percentage from 45% to 55% by weight.

12. The composition according to claim 1 wherein said resin incense extract is in a percentage from 20% to 30% by weight, wherein said polysaccharides and/or plant extracts comprising polysaccharides are in a percentage from 7% to 13% by weight, and wherein said antioxidants and/or plant extracts comprising antioxidants are in a percentage from 45% to 55% by weight.

13. A daily dosage unit of a composition for treatment of irritable bowel syndrome (IBS) in a form suitable for oral administration, comprising:
   approximately 500-800 mg of lyophilised resin incense extract,
   180-300 mg of dehydrated Aloe vera leaf gel,
   70-170 mg of lyophilised chamomile flower extract,
   800-1250 mg of lemon-balm leaf,
   40-60 mg of fennel essential oil, and
   270-400 mg of cumin fruit or seed powder;
   which is effective for producing a barrier effect on intestinal mucosa and increasing adhesivity of said barrier effect to intestinal mucosa.

14. The dosage unit according to claim 13 further comprising a natural or plant derived compound having an activity suitable for relieving a symptom of irritable bowel syndrome (IBS), wherein said natural or plant derived compound is selected from the group consisting of gentian root extract, boldo leaf extract, milk thistle fruit extract, artichoke leaves extract, dandelion root extract, anise fruit extract, rosemary leaf extract, mint leaf extract, marjoram leaf extract, cumin fruit extract, cumin seed extract, coriander fruit extract, ginger root extract, fennel fruit extract, caraway fruit extract, plant charcoal, and inulin.

15. A medical device, dietary supplement, or medical food for relief of a symptom of irritable bowel syndrome (IBS) comprising:
   approximately 500-800 mg of lyophilised resin incense extract,
   180-300 mg of dehydrated Aloe vera leaf gel,
   70-170 mg of lyophilised chamomile flower extract,
   800-1250 mg of lemon-balm leaf,
   40-60 mg of fennel essential oil, and
   270-400 mg of cumin fruit or seed powder;
   which is effective for producing a barrier effect on intestinal mucosa and increasing adhesivity of said barrier effect to intestinal mucosa.

16. A method for preparation of a dosage unit according to claim 13, comprising admixing together said resin incense extract, said Aloe vera leaf gel, said chamomile flower extract, said lemon-balm leaf, said fennel essential oil, and said cumin fruit or seed powder; together with further excipients.

17. A method for preparation of a dosage unit according to claim 14, comprising admixing together said resin incense extract, said Aloe vera leaf gel, said chamomile flower extract, said lemon-balm leaf, said fennel essential oil, said cumin fruit or seed powder, and said natural or plant derived compound; together with further excipients.

18. A method for treatment of a patient suffering from irritable bowel syndrome (IBS), comprising administering a composition according to claim 13 to a patient in need thereof.

19. A method for treatment of a patient suffering from irritable bowel syndrome (IBS), comprising administering a composition according to claim 14 to a patient in need thereof.

* * * * *